(12) United States Patent
Jones et al.

(10) Patent No.: US 7,544,749 B2
(45) Date of Patent: Jun. 9, 2009

(54) POLYMERIZATION CATALYSTS, ORGANIC TRANSITION METAL COMPOUNDS, PROCESS FOR PREPARING POLYOLEFINS AND POLYOLEFINS

(75) Inventors: Robert L. Jones, Frankfurt (DE); Naka Seidel, Frankfurt (DE); Michael J. Elder, Columbia, MD (US); John A. Ewen, Lake Placid, FL (US)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/543,961

(22) PCT Filed: Feb. 5, 2004

(86) PCT No.: PCT/EP2004/001050

§ 371 (c)(1),
(2), (4) Date: Aug. 10, 2005

(87) PCT Pub. No.: WO2004/069881

PCT Pub. Date: Aug. 19, 2004

(65) Prior Publication Data

US 2006/0100092 A1     May 11, 2006

Related U.S. Application Data

(60) Provisional application No. 60/454,482, filed on Mar. 13, 2003.

(30) Foreign Application Priority Data

Feb. 7, 2003    (DE) ................................ 103 05 227

(51) Int. Cl.
*C08F 4/72*     (2006.01)
*C08F 4/64*     (2006.01)

(52) U.S. Cl. .................. 526/172; 526/161; 526/351

(58) Field of Classification Search .......... 526/172, 526/161, 351; 556/51, 57, 42
See application file for complete search history.

(56) References Cited

U.S. PATENT DOCUMENTS 6,121,182 A     9/2000   Okumura et al.

(Continued)

FOREIGN PATENT DOCUMENTS

EP     0 834 519     4/1998

(Continued)

OTHER PUBLICATIONS

JP 2002-179724 (abstract and translation in English).*

(Continued)

*Primary Examiner*—David Wu
*Assistant Examiner*—Rip A. Lee

(74) *Attorney, Agent, or Firm*—William R. Reid

(57) ABSTRACT

A catalyst system obtained by reacting at least one chiral transition metal compound and at least one cocatalyst, where the chiral transition metal compound is a transition metal compound of formula (Ia) or one of its enantiomers of the formula (Ia*), (Ia)

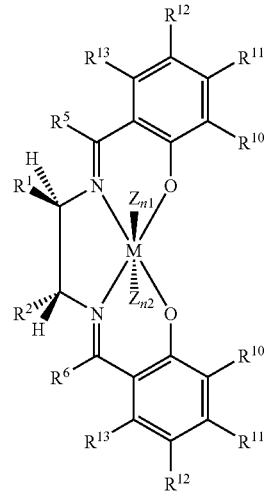

(Ia*)

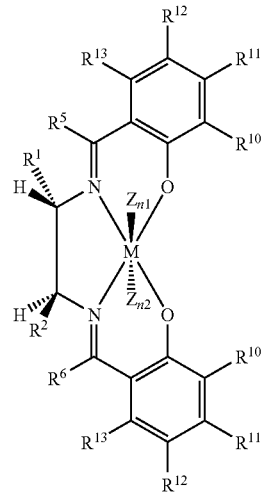

Figure 1A:
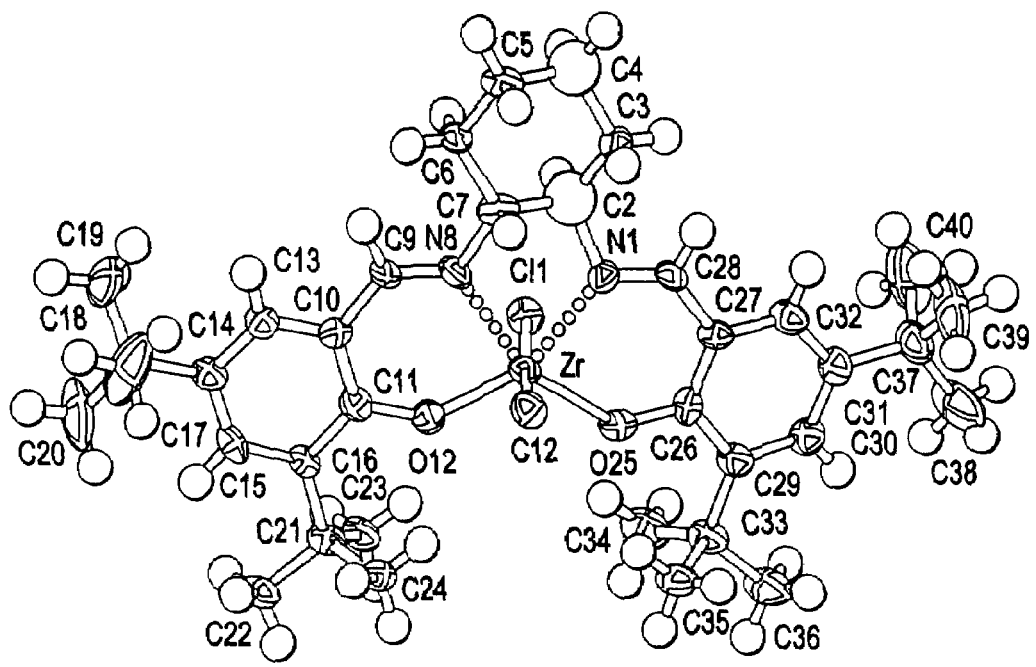

where
M is an element of Group 4,
Z are each halogen, hydrogen, $C_1$-$C_{10}$-alkyl, $C_6$-$C_{14}$-aryl, alkylaryl or arylalkyl having from 1 to 4 carbon atoms in the alkyl part and from 6 to 10 carbon atoms in the aryl part,
n1 and n2 are each 0 or 1,
$R^1$ and $R^2$ are each a $C_1$-$C_{40}$ radical, or $R^1$ and $R^2$ together with the atoms connecting them form a cyclic or polycyclic ring system,
$R^5$ and $R^6$ are each hydrogen or a $C_1$-$C_{40}$ radical,
$R^{10}$, $R^{11}$ are each hydrogen, t-butyl or phenyl,
$R^{12}$ are each t-butyl or phenyl, and
$R^{13}$ are each hydrogen or a $C_1$-$C_{40}$ radical.

8 Claims, 2 Drawing Sheets

U.S. PATENT DOCUMENTS

| | | | |
|---|---|---|---|
| 6,309,997 B1 * | 10/2001 | Fujita et al. | 502/167 |
| 6,417,302 B1 | 7/2002 | Bohnen | |
| 6,589,905 B1 | 7/2003 | Fischer et al. | |
| 6,812,185 B2 | 11/2004 | Fischer et al. | |

FOREIGN PATENT DOCUMENTS

| | | | |
|---|---|---|---|
| JP | 2002-179724 | * | 6/2002 |
| JP | 2002-308843 | * | 10/2002 |
| JP | 2002-338616 | * | 11/2002 |
| JP | 2002-268030 | * | 9/2003 |
| WO | WO-91/09882 | | 7/1991 |
| WO | WO-96/00243 | | 1/1996 |
| WO | WO-98/40419 | | 9/1998 |
| WO | WO-99/06414 | | 2/1999 |
| WO | WO-99/56699 | | 11/1999 |
| WO | WO-00/05277 | | 2/2000 |
| WO | WO-00/31090 | | 6/2000 |
| WO | WO 02/12171 A1 * | | 2/2002 |
| WO | WO-02/16455 | | 2/2002 |

OTHER PUBLICATIONS

Belokon et al. J. Am. Chem. Soc. 1999, 121, 3968-3973.*
Bruns, S.; Haufe, G. J. Fluorine Chemistry 2000, 104, 247-254.*
JP 2002-308843 (Oct. 23, 2002); abstract and translation in English.*
JP 2002-338616, Nov. 27, 2002 (abstract and translation in English).*
Repo et al. Macromolecules 1997, 30, 171-175.*
Repo, T. et al., "Ethylenebis(salicylideneiminato)zirconium Dichloride: Crystal Structure And Use As A Heterogeneous Catalyst In The Polymerization Of Ethylene", Macromolecules (2000), 30, pp. 171-175.
Knight, P. et al., "Problems And Solutions For Alkene Polymerisation Catalysts Incorporating Schiff-bases; Migratory Insertion And Radical Mechanisms of Catalyst Deactivation", Chem Commun (2002), pp. 352-353.
Makio, H. et al., "FI Catalysts: A New Family Of High Performance Catalysts For Olefin Polymerization", Adv. Synth. Catal. (2002), 344, 5, pp. 477-493.

* cited by examiner

13C-NMR

POLYMERIZATION CATALYSTS, ORGANIC TRANSITION METAL COMPOUNDS, PROCESS FOR PREPARING POLYOLEFINS AND POLYOLEFINS

RELATED APPLICATIONS

This application is a national stage application (under 35 U.S.C. 371) of PCT/EP2004/001050 filed Feb. 5, 2004 which claims benefit to German application 103 05 227.5 filed Feb. 7, 2003 and U.S. provisional application 60/454,482 filed Mar. 13, 2003.

The present invention relates to catalyst systems for preparing isotactic polyolefins obtainable by reacting at least one chiral transition metal compound and at least one cocatalyst which is able to convert the chiral transition metal compound into a cation, where the chiral transition metal compound contains two bidentate chelating ligands connected to one another via a bridge and, if desired, one or two further monodentate ligands, with the four coordinating atoms of the two chelating ligands being in an approximately planar arrangement around the transition metal ion and up to two further ligands being located above and below this approximately planar coordination sphere formed by the four coordinating atoms of the two chelating ligands and, in the case of two such further ligands, these being in the trans position relative to one another.

In addition, the present invention provides for the use of the catalyst systems of the present invention for preparing polyolefins, provides a process for preparing polyolefins by polymerization or copolymerization of at least one olefin in the presence of one of the catalyst systems of the present invention, provides for the use of chiral transition metal compounds for preparing a catalyst system for the polymerization of olefins, provides chiral transition metal compounds, provides a process for preparing a catalyst system for olefin polymerization, provides a process for preparing isotactic polyolefins, provides polyolefins obtainable by a process according to the present invention, provides polyolefin compositions comprising the polyolefins of the present invention and provides products produced from such polyolefin compositions.

Research and development on the use of organic transition metal compounds, in particular metallocenes, as catalyst components for the polymerization and copolymerization of olefins with the aim of preparing tailored polyolefins has been pursued intensively in universities and in industry over the past 15 years.

Apart from metallocenes, new classes of transition metal compounds which do not contain any cyclopentadienyl ligands are now being examined to an increasing extent as catalyst components.

Macromolecules 1997, 30, 171-175, discloses ethylenebis(salicylideniminato)zirconium dichloride and its use as catalyst component in the polymerization of ethylene. The polymerization of higher α-olefins such as propylene was not examined.

Adv. Synth. Catal. 2002, 344, No. 5, describes transition metal complexes of metals of group 4 of the Periodic Table of the Elements with phenoxyimine ligands. In these complexes, the transition metal ion is surrounded by an octahedral arrangement of two phenoxyimine ligands and two chloride ions, with the two oxygen atoms being in the trans-position and the two nitrogen atoms and the two chlorine atoms being in the cis-position relative to one another. Polypropylenes having different tacticities depending on the cocatalyst and on the substitution pattern of the phenoxyimine ligands are described. While a highly syndiotactic polypropylene is described, only atactic polypropylene and an isotactic polypropylene having a low melting point and a low isotacticity were obtained using the catalyst systems disclosed.

Chem. Commun., 2002, 352-353, describes transition metal complexes bearing, in each case, a biaryl-bridged bisphenoxyimine ligand and two chlorine ligands, their use in ethylene polymerization and possible deactivation of the catalyst. The transition metal complexes of titanium and zirconium which are described have a structure in which the metal ion is octahedrally coordinated and the two oxygen atoms are in the trans position and the two nitrogen atoms and the two chlorine atoms are in the Cis-position relative to one another.

WO 99/56699 lists various chiral bis(salicylidene)-1,2-diaminocyclohexane-transition metal complexes, some of which are commercially available. No olefin polymerizations are described.

JP2002-179724 describes the polymerization of ethylene using a catalyst system consisting of N,N'-bis-(3,5-di-tert-butylsalicylidene)-1,2-diaminocyclohexanemanganese(III) chloride and methylaluminoxane (MAO). JP2002-179724 does not comment on the geometry of the transition metal complex.

It is an object of the present invention to find catalyst systems based on nonmetallocenes which make it possible to prepare highly isotactic polyolefins, in particular isotactic polypropylenes having melting points above 150° C. Furthermore, the catalyst systems should display good activities and be able to be used at industrially relevant polymerization temperatures.

We have found that this object is achieved by the catalyst systems mentioned at the outset.

The chiral transition metal compound contains a metal cation of an element of group 3, 4, 5, 6, 7, 8, 9, 10, 11 or 12 of the Periodic Table of the Elements or a lanthanide element, for example scandium, yttrium, titanium, zirconium, hafnium, vanadium, niobium, tantalum, chromium, molybdenum, tungsten, manganese, iron, cobalt, nickel, palladium, copper or zinc. Preference is given to a metal cation of an element of group 3, 4, 5 or 6 of the Periodic Table of the Elements or a lanthanide element, in particular to a metal cation of an element of group 4 or 6 of the Periodic Table of the Elements, for example titanium, zirconium, hafnium or chromium, preferably zirconium, hafnium or chromium.

The bridge in the chiral transition metal compound is preferably a chiral bridge, in particular a bridge containing two chiral $sp^3$-hybridized carbon atoms which are each joined directly to one of the two chelating ligands. Particular preference is given to a bridge in which the two chiral $sp^3$-hybridized carbon atoms are joined directly to one another.

Each of the two bidentate chelating ligands preferably bears a single negative charge. The two coordinating atoms of the chelating ligands are, for example, nitrogen, phosphorus, oxygen, sulfur, selenium or tellurium, in particular nitrogen, oxygen or sulfur. Preference is given to at least one, in particularly precisely one, of the two coordinating atoms of the bidentate chelating ligand being a nitrogen atom. Particular preference is given to a bidentate chelating ligand having one coordinating nitrogen atom and one coordinating oxygen atom.

A bidentate chelating ligand which forms a five-membered or six-membered, in particular six-membered, metallacycle with the metal ion is also preferred.

Preference is also given to bidentate chelating ligands which are bridged to one another via one of the two coordinating atoms, in particular via a nitrogen atom.

Particular preference is given to bidentate chelating ligands having an imine function derived from 1,3-dicarbonyl compounds, for example acetylacetone, benzoylacetone or 1,3-diphenyl-1,3-propanedione and substituted derivatives thereof, or derived from ortho-carbonylphenol derivatives, e.g. 2-hydroxybenzaldehyde or 2-hydroxyacetophenone or substituted derivatives thereof, with the imine function being formed by reaction of a carbonyl function with a primary amine. The monodentate ligands are singly negatively charged anions, in particular halide anions, such as fluoride, chloride, bromide or iodide anions, in particular chloride anions, hydride anions, $C_1$-$C_{40}$-hydrocarbon anions, such as methyl, tert-butyl, vinyl, phenyl or benzyl anions, alkoxy or aryloxy anions such as methoxy or phenoxy anions and amide anions such as dimethylamide anions. Particularly preferred monodentate ligands are chloride, methyl and benzyl anions, in particular chloride anions.

The four coordinating atoms of the two bidentate chelating ligands are in an approximately planar arrangement around the transition metal ion. The transition metal ion does not need to lie exactly in the plane formed by the four coordinating atoms of the two bidentate chelating ligands. For the purposes of the present invention, approximately planar means that the four coordinating atoms of the two chelating ligands do not have to lay exactly in a plane, but the two coordinating atoms of the first chelating ligand can be slightly twisted relative to the two coordinating atoms of the second chelating ligand. In the present case, an approximately planar arrangement of the four coordinating atoms of the two chelating ligands around the metal ion means that the angle between a first plane formed by the two coordinating atoms of the first chelating ligand and the transition metal ion and a second plane formed by the two coordinating atoms of the second chelating ligand and the transition metal ion is in the range from 0° to 20°, in particular in the range from 0° to 10°.

Preference is given to catalyst systems as described above in which the chiral transition metal compound is a transition metal compound of the formula (I) or one of its enantiomers of the formula (I*)

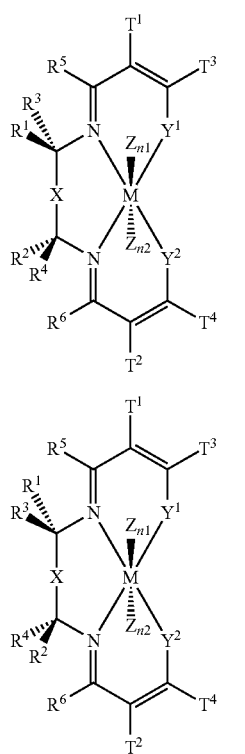

where

M is an element of group 3, 4, 5, 6, 7, 8, 9, 10, 11 or 12 of the Periodic Table of the Elements or the lanthanides, Z may be identical or different and are each an organic or inorganic anionic ligand, n1, n2 may be identical or different and are each 0 or 1, where n1+n2+2 corresponds to the valence of M, $R^1$ and $R^2$ may be identical or different and are each a $C_1$-$C_{40}$ radical, or $R^1$ and $R^2$ together with the atoms connecting them form a cyclic or polycyclic ring system which may contain one or more, identical or different heteroatoms selected from the group consisting of the elements N, O, P, S and Si in place of carbon atoms in the ring system, $R^3$ is hydrogen or a $C_1$-$C_{40}$ radical, where $R^3$ displays lower steric hindrance than $R^1$, $R^4$ is hydrogen or a $C_1$-$C_{40}$ radical, where $R^4$ displays lower steric hindrance than $R^2$, $R^5$ and $R^6$ may be identical or different and are each hydrogen or a $C_1$-$C_{40}$ radical, or $R^1$ and $R^3$, $R^2$ and $R^4$, $R^1$ and $R^5$ and/or $R^2$ and $R^6$ together with the atoms connecting them in each case form a cyclic or polycyclic ring system which may contain one or more, identical or different heteroatoms selected from the group consisting of the elements N, O, P, S and Si in place of carbon atoms in the ring system, X is a single bond between the two carbon atoms or is a divalent group, $Y^1$, $Y^2$ may be identical or different and are each oxygen, sulfur, selenium, tellurium, an $NR^9$ group or a $PR^9$ group, $R^7$, $R^8$, $R^9$ may be identical or different and are each hydrogen, $C_1$-$C_{20}$-alkyl, $C_2$-$C_{20}$-alkenyl, $C_6$-$C_{22}$-aryl, alkylaryl or arylalkyl having from 1 to 10 carbon atoms in the alkyl part and from 6 to 22 carbon atoms in the aryl part, $T^1$, $T^2$, $T^3$ and $T^4$ may be identical or different and are each hydrogen or a $C_1$-$C_{40}$ radical, or $T^1$ and $T^3$ and/or $T^2$ and $T^4$ together with the carbon atoms connecting them in each case form a cyclic or polycyclic ring system which may contain one or more, identical or different heteroatoms selected from the group consisting of the elements N, O, P, S and Si in place of carbon atoms in the ring system.

$M^1$ is an element of group 3, 4, 5, 6, 7, 8, 9, 10, 11 or 12 of the Periodic Table of the Elements or the lanthanides, for example scandium, yttrium, titanium, zirconium, hafnium, vanadium, niobium, tantalum, chromium, molybdenum, tungsten, manganese, iron, cobalt, nickel, palladium, copper or zinc. Preference is given to a metal cation of an element of group 3, 4, 5 or 6 of the Periodic Table of the Elements or a lanthanide element, in particular to a metal cation of an element of group 4 or 6 of the Periodic Table of the Elements, for example titanium, zirconium, hafnium or chromium, preferably zirconium, hafnium and chromium and particularly preferably zirconium.

The radicals Z can be identical or different, preferably identical, and are each an organic or inorganic anionic ligand. Z is preferably halogen, for example fluorine, chlorine, bromine or iodine, in particular chlorine, hydrogen, $C_1$-$C_{20}$—, preferably $C_1$-$C_4$-alkyl, $C_2$-$C_{20}$—, preferably $C_2$-$C_4$-alkenyl, $C_6$-$C_{22}$—, preferably $C_6$-$C_{10}$-aryl, alkylaryl or arylalkyl having from 1 to 10, preferably from 1 to 4, carbon atoms in the alkyl part and from 6 to 22, preferably from 6 to 10, carbon atoms in the aryl part, —$OR^7$ or $NR^7R^8$. Z is particularly preferably chlorine or methyl.

n1, n2 may be identical or different and are each 0 or 1, with n1+n2+2 corresponding to the valence of M. Preference is given to n1 and n2 being identical and each equal to one for the elements of group 4 of the Periodic Table of the Elements, so as to give an oxidation number of +4, and being identical and each equal to 0 for the elements of group 10 of the Periodic Table of the Elements, so as to give an oxidation number of +2.

$R^1$ and $R^2$ may be identical or different preferably identical, and are each a $C_1$-$C_{40}$ radical such as a $C_1$-$C_{40}$-hydrocarbon radical or $C_3$-$C_{40}$—$SiCR^7)_3$, or $R^1$ and $R^2$ together with the atoms connecting them form a cyclic or polycyclic ring system which may contain one or more, identical or different heteroatoms selected from the group consisting of the elements N, O, P, S and Si, preferably N, O and S, in particular N, in place of carbon atoms in the ring system. Preference is given to $R^1$ and $R^2$ each being a cyclic, branched or unbranched $C_1$-$C_{20}$—, preferably $C_1$-$C_8$-aryl radical, a $C_2$-$C_{20}$—, preferably $C_2$-$C_8$-alkenyl radical, a $C_6$-$C_{22}$, preferably $C_6$-$C_{10}$-aryl radical, an alkylaryl or arylalkyl radical having from 1 to 4, carbon atoms in the alkyl part and from 6 to 22, preferably from 6 to 10, carbon atoms in the aryl part, with the radicals also being able to be halogenated, or $C_3$-$C_{18}$—, preferably $C_3$-$C_8$—$Si(R^7)_3$, or $R^1$ and $R^3$ together with the atoms connecting them forming a cyclic 4- to 8-membered, preferably 5- or 6-membered, ring system which may in turn bear $C_1$-$C_{20}$ radicals. Particular preference is given to $R^1$ and $R^2$ each being a cyclic, branched or unbranched $C_1$-$C_8$-alkyl radical, a $C_8$-$C_{10}$-aryl radical, an alkylaryl or arylalkyl radical having from 1 to 4 carbon atoms in the alkyl part and from 6 to 10 carbon atoms in the aryl part or trimethysilyl or $R^1$ and $R^2$ together with the atoms connecting them forming a cyclic 5- or 6-membered ring system which may in turn bear cyclic, branched or unbranched $C_1$-$C_8$-alkyl radicals, $C_6$-$C_{10}$-aryl radicals, alkylaryl or arylalkyl radicals having from 1 to 4 carbon atoms in the alkyl part and from 6 to 10 carbon atoms in the aryl part or trimethylsilyl radicals. Examples of particularly preferred radicals $R^1$ and $R^2$ are methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl. Examples of particularly preferred ring systems formed from the radicals $R^1$ and $R^2$ and the atoms connecting them are 1,2-cyclohexylene, 1,2-cyclopentylene and 1-benzylpyrrolidin-3,4-ylene.

$R^3$ is hydrogen or a $C_1$-$C_{40}$ radical such as a $C_1$-$C_{40}$ hydrocarbon radical or $C_3$-$C_{40}$—$Si(R^7)_3$, where $R^3$ displays a lower steric hindrance than $R^1$. $R^3$ is preferably hydrogen, a cyclic, branched or un-branched, in particular unbranched, $C_1$-$C_{20}$—, preferably $C_1$-$C_8$-alkyl radical, a $C_2$-$C_{20}$—, preferably $C_2$-$C_8$-alkenyl radical, a $C_8$-$C_{22}$—, preferably $C_6$-$C_{10}$-aryl radical, an alkylaryl or arylalkyl radical, preferably an arylalkyl radical, having from 1 to 10, preferably from 1 to 4, carbon atoms in the alkyl part and from 6 to 22, preferably from 6 to 10, carbon atoms in the aryl part, with the radicals also being able to be halogenated. Particular preference is given to $R^3$ being hydrogen or an un-branched $C_1$-$C_8$-alkyl radical. $R^3$ is very particularly preferably hydrogen.

$R^4$ is hydrogen or a $C_1$-$C_{40}$ radical such as a $C_1$-$C_{40}$-hydrocarbon radical or $C_3$-$C_{40}$—$Si(R^7)_3$, where $R^4$ displays a lower steric hindrance than $R^2$. $R^4$ is preferably hydrogen, a cyclic, branched or un-branched, in particular unbranched, $C_1$-$C_{20}$—, preferably $C_1$-$C_6$-alkyl radical, a $C_2$-$C_{20}$—, preferably $C_2$-$C_6$-alkenyl radical, a $C_6$-$C_{22}$—, preferably $C_6$-$C_{10}$-aryl radical, an alkylaryl or arylalkyl radical, preferably an arylalkyl radical, having from 1 to 10, preferably from 1 to 4, carbon atoms in the alkyl part and from 6 to 22, preferably from 6 to 10, carbon atoms in the aryl part, with the radicals also being able to be halogenated. Particular preference is given to $R^4$ being hydrogen or an un-branched $C_1$-$C_8$-alkyl radical. $R^4$ is very particularly preferably hydrogen.

The steric hindrance displayed by a radical is determined by the space which it occupies. For example, the steric hindrance increases in the following order:

Hydrogen<methyl<ethyl<isopropyl<tert-butyl.

$R^5$ and $R^6$ may be identical or different, in particular identical, and are each hydrogen or a $C_1$-$C_{40}$ radical. $R^6$ and $R^6$ are preferably hydrogen, a cyclic, branched or unbranched $C_1$-$C_{20}$—, preferably $C_1$-$C_8$-alkyl radical, a $C_2$-$C_{20}$—, preferably $C_2$-$C_8$-alkenyl radical, a $C_6$-$C_{22}$—, preferably $C_6$-$C_{10}$-aryl radical, an alkylaryl or arylalkyl radical having from 1 to 10, preferably from 1 to 4, carbon atoms in the aryl part, and from 6 to 22, preferably from 6 to 10, carbon atoms in the aryl part, with the radicals also being able to be halogenated. Particular preference is given to $R^5$ and $R^6$ each being hydrogen, a cyclic, branched or unbranched $C_1$-$C_8$-alkyl radical, a $C_6$-$C_{10}$-aryl radical, an alkylaryl or arylalkyl radical having from 1 to 4 carbon atoms in the alkyl part and from 6 to 10 carbon atoms in the aryl part. Examples of particularly preferred radicals $R^5$ and $R^6$ are hydrogen, methyl, ethyl, n-propyl, isopropyl n-butyl, i-butyl, s-butyl, t-butyl, n-pentyl, cyclopentyl, n-hexyl, cyclohexyl, n-heptyl, n-octyl, benzyl, 2-phenylethyl, phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, in particular hydrogen.

Furthermore, it is also possible for in each case two radicals $R^1$ and $R^3$, $R^2$ and $R^4$, $R^1$ and $R^5$ and/or $R^2$ and $R^6$ together with the atoms connecting them to form a cyclic or polycyclic ring system which may contain one or more, identical or different heteroatoms selected from the group consisting of the elements N, O, P, S and Si, in particular N, O and S, in place of carbon atoms in the ring system.

X is a single bond between the two carbon atoms or is a divalent group. Examples of divalent groups X are $CR^7R^8$, in particular $CH_2$, $CR^7R^8$—$CR^7R^8$, in particular $CH_2$—$CH_2$, $(CR^7R^8)_3$, $(CR^7R^8)_4$ or $(CR^7R^8)_5$. X is preferably a single bond or $CH_2$, in particular a single bond.

$Y^1$ and $Y^2$ may be identical or different, in particular identical, and are each oxygen, sulfur, selenium, tellurium, an $NR^9$ group or a $PR^9$ group, in particular oxygen.

$R^7$, $R^8$ and $R^9$ may be identical or different and are each hydrogen, $C_1$-$C_{20}$—, preferably $C_1$-$C_4$-alkyl, $C_2$-$C_{20}$—, preferably $C_2$-$C_4$-alkenyl, $C_6$-$C_{22}$—, preferably $C_6$-$C_{10}$-aryl, alkylaryl or arylalkyl having from 1 to 10, preferably from 1 to 4, carbon atoms in the alkyl part and from 6 to 22, preferably from 6 to 10, carbon atoms in the aryl part.

$T^1$, $T^2$, $T^3$ and $T^4$ may be identical or different and are each hydrogen or a $C_1$-$C_{40}$ radical, or $T^1$ and $T^3$ and/or $T^2$ and $T^4$ together with the carbon atoms connecting them in each case form a cyclic or polycyclic ring system which may contain one or more, identical or different heteroatoms selected from the group consisting of the elements N, O, P, S and Si in place of carbon atoms in the ring system. Preference is given to $T^1$, $T^2$, $T^3$ and $T^4$ each being a cyclic, branched or unbranched $C_1$-$C_{20}$—, preferably $C_1$-$C_8$-alkyl radical, a $C_2$-$C_{20}$—, preferably $C_2$-$C_8$-alkenyl radical, a $C_6$-$C_{22}$—, preferably $C_6$-$C_{10}$-aryl radical, an alkylaryl or arylalkyl radical having from 1 to 10, preferably from 1 to 4, carbon atoms in the alkyl part and from 6 to 22, preferably from 6 to 10, carbon atoms in the aryl part, with the radicals also being able to be halogenated, or $T^1$ and $T^3$ and/or $T^2$ and $T^4$ together with the carbon atoms connecting them in each case forming substituted or unsubstituted, aromatic or partially hydrogenated 5- to 8-membered, in particular 5- or 6-membered, ring systems which may contain heteroatoms selected from the group consisting of O, S and N and may in turn be part of larger polycyclic ring systems. Particular preference is given to $T^1$ and $T^3$ and $T^2$ and $T^4$ together with the two connecting carbon atoms forming substituted or unsubstituted phenyl rings, thiophene rings or pyrrole rings, in particular phenyl rings, which may in turn be part of larger polycyclic ring systems.

The radicals $R^1$, $R^2$, $R^3$, $R^4$, $R^5$, $R^6$, $R^7$, $R^8$, $R^9$, $T^1$, $T^2$, and $T^4$ may, according to the present invention, also contain functional groups without altering the polymerization properties of the catalyst system of the present invention as long as these functional groups are chemically inert under the polymerization conditions.

Furthermore, the substituents are, for the purposes of the present invention, defined as follows unless restricted further:

The term "$C_1$-$C_{40}$ radical" as used in the present text refers to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals. $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-alkyl radicals or $C_8$-$C_{40}$-arylalkenyl radicals.

The term "alkyl" as used in the present text encompasses linear or singly or multiply branched saturated hydrocarbons which may also be cyclic. Preference is given to $C_1$-$C_{16}$-alkyl, such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, sec-butyl or tert-butyl.

The term "alkenyl" as used in the present text encompasses linear or singly or multiplicably branched hydrocarbons having one or more C—C double bonds which may be cumulated or alternating.

The term "saturated heterocyclic radical" as used in the present text refers to monocyclic or polycyclic, substituted or unsubstituted hydrocarbon radicals in which one or more carbon atoms, CH groups and/or $CH_2$ groups are replaced by heteroatoms selected from the group consisting of O, S N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothienyl and the like, and also derivatives thereof which are substituted by methyl, ethyl, propyl, isopropyl and tert-butyl radicals.

The term "aryl" as used in the present text refers to aromatic and fused or unfused polyaromatic hydrocarbon substituents which may be unsubstituted or monosubstituted or polysubstituted by linear or branched $C_1$-$C_{18}$-alkyl, $C_1$-$C_{18}$-alkoxy, $C_2$-$C_{10}$-alkenyl or $C_3$-$C_{15}$-alkylalkenyl. Preferred examples of substituted and unsubstituted aryl radicals are, in particular, phenyl, pentafluorophenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to aromatic hydrocarbon substituents in which one or more carbon atoms are replaced by nitrogen, phosphorus, oxygen or sulfur atoms or combinations thereof. These can, like the aryl radicals, be unsubstituted or mono-substituted or polysubstituted by linear or branched $C_1$-$C_{18}$-alkyl, $C_2$-$C_{10}$-alkenyl or $C_3$-$C_{15}$-alkylalkenyl. Preferred examples are furyl, thienyl, pyrrolyl, pyridyl, pyrazolyl, imidazolyl, oxazolyl, thiazolyl, pyrimidinyl, pyrazinyl and the like, and also derivatives thereof which are substituted by methyl, ethyl, propyl, isopropyl and tert-butyl radicals.

The term "alkylalkenyl" as used in the present text encompasses linear or singly or multiplicably branched hydrocarbons having one or more C—C double bonds which are isolated so that the substituent has both alkyl and alkenyl sections.

The term "arylalkyl" as used in the present text refers to aryl-containing substituents whose aryl radical is linked via an alkyl chain to the remainder of the molecule. Preferred examples are benzyl, substituted benzyl, phenethyl, substituted phenethyl, and the like.

The terms fluoroalkyl and fluoroaryl mean that at least one hydrogen atom, preferably more than one hydrogen atoms up to a maximum of all hydrogen atoms, of the respective substituent has/have been replaced by fluorine atoms. Examples of fluorine-containing substituents which are preferred according to the present invention are trifluoromethyl, 2,2,2-trifluoroethyl, pentafluorophenyl, 4trifluoromethylphenyl, 4-perfluoro-tert-butylphenyl and the like.

Particular preference is given to catalyst systems as described above in which the chiral transition metal compound of the formula (I) or (I*) is a transition metal compound of the formula (Ia) or one its enantiomers of the formula (Ia*),

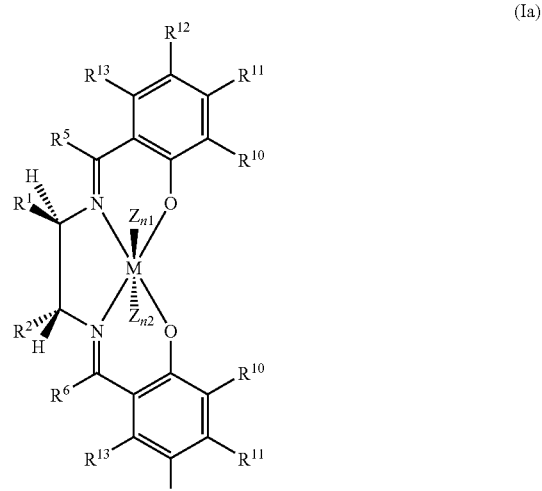

(Ia)

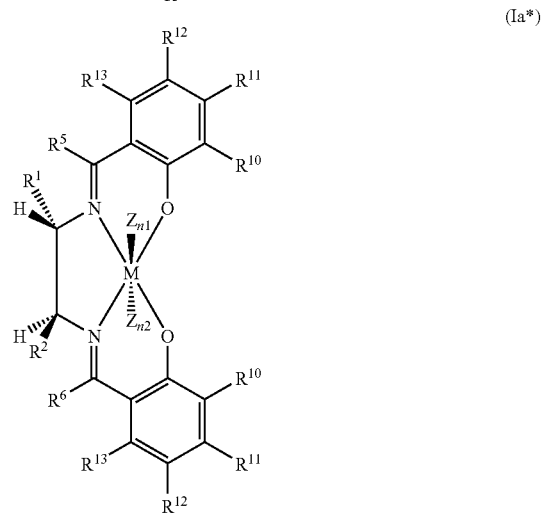

(Ia*)

where

M is an element of group 4 or 6 of the Periodic Table of the Elements,

Z may be identical or different and are each halogen, hydrogen, $C_1$-$C_{10}$-alkyl, $C_8$-$C_{14}$-aryl, alkylaryl or arylalkyl having from 1 to 4 carbon atoms in the alkyl part and from 6 to 10 carbon atoms in the aryl part, n1, n2 may be identical or different and are each 0 or 1, with n1+n2+2 corresponding to the valence of M, $R^1$ and $R^2$ may be identical or different and are each a $C_1$-$C_{40}$ radical, or $R^1$ and $R^2$ together with the atoms connecting them form a cyclic or polycyclic ring system which may contain one or more, identical or different heteroatoms selected from the group consisting of the elements N, O, P, S and Si in place of carbon atoms in the ring system, $R^5$ and $R^6$ are identical and are each hydrogen or a $C_1$-$C_{40}$ radical, $R^{10}$, $R^{11}$, $R^{12}$ and $R^{13}$ may be identical or different and are each hydrogen or a $C_1$-$C_{40}$ radical, or two adjacent radicals $R^{10}$, $R^{11}$, $R^{12}$ and $R^{13}$ together with the two connecting carbon atoms may form a cyclic ring system.

$M^1$ is a element of group 4 or 6 of the Periodic Table of the Elements, for example titanium, zirconium hafnium, chromium, molybdenum or tungsten, preferably titanium, zirconium, hafnium or chromium, particularly preferably zirconium or hafnium, and very particularly preferably zirconium.

The radicals Z may be identical or different, preferably identical, and are each halogen, for example fluorine, chlorine, bromine or iodine, in particular chlorine, hydrogen, $C_1$-$C_{10}$—, preferably $C_1$-$C_4$-alkyl, $C_6$-$C_{14}$—, preferably $C_6$-$C_{10}$-aryl or alkylaryl or arylalkyl having from 1 to 4 carbon atoms in the alkyl part and from 6 to 10, preferably 6, carbon atoms in the aryl part. Z is preferably chlorine, benzyl or methyl, in particular chlorine.

The radicals $R^1$ and $R^2$ may be identical or different, in particular identical, and are each a $C_1$-$C_{40}$ radical such as a $C_1$-$C_{40}$-hydrocarbon radical or $C_3$-$C_{40}$—Si($R^7$)$_3$, or $R^1$ and $R^2$ together with the atoms connecting them form a cyclic or polycyclic, in particular monocyclic ring system which may contain one or more, identical or different heteroatoms selected from the group consisting of the elements N, O, P, S and Si, preferably N, O and S, in particular N, in place of carbon atoms in the ring system. Preference is given to $R^1$ and $R^2$ each being a cyclic, branched or unbranched $C_1$-$C_{20}$—, preferably $C_1$-$C_8$-alkyl radical, a $C_2$-$C_{20}$—, preferably $C_2$-$C_8$-alkenyl radical, a $C_8$-$C_{22}$—, preferably $C_6$-$C_{10}$-aryl radical, an alkylaryl or arylalkyl radical having from 1 to 10, preferably from 1 to 4, carbon atoms in the alkyl part and from 6 to 22, preferably from 6 to 10, carbon atoms in the aryl part, with the radicals also being able to be halogenated, or $C_3$-$C_{18}$—, preferably $C_3$-$C_6$—Si($R^7$)$_3$, or $R^1$ and $R^2$ together with the atoms connecting them forming a cyclic 4- to 8-membered, preferably 5- or 6-membered, ring system which may in turn bear $C_1$-$C_{20}$ radicals. Particular preference is given to $R^1$ and $R^2$ each being a cyclic, branched or unbranched $C_1$-$C_8$-alkyl radical, a $C_8$-$C_{10}$-aryl radical, an alkylaryl or arylalkyl radical having from 1 to 4 carbon atoms in the alkyl part and from 6 to 10 carbon atoms in the aryl part or trimethylsilyl or $R^1$ and $R^2$ together with the atoms connecting them forming a cyclic 5- or 6-membered ring system which may in turn bear cyclic, branched or unbranched $C_1$-$C_8$-alkyl radicals, $C_6$-$C_{10}$-aryl radicals, alkylaryl or arylalkyl radicals having from 1 to 4 carbon atoms in the alkyl part and from 6 to 10 carbon atoms in the aryl part or trimethylsilyl radicals. Examples of particularly preferred radicals $R^1$ and $R^2$ are methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl. Examples of particularly preferred ring systems formed from the radicals $R^1$, $R^2$ and the atoms connecting them are 1,2-cyclohexylene, 1,2-cyclopentylene and 1-benzylpyrrolidin-3,4-ylene.

The radicals $R^5$ and $R^8$ are identical and are each hydrogen or a $C_1$-$C_{40}$ radical. $R^5$ and $R^6$ are preferably each hydrogen, a cyclic, branched or unbranched $C_1$-$C_{20}$—, preferably $C_1$-$C_8$-alkyl radical, a $C_6$-$C_{22}$—, preferably $C_6$-$C_{10}$-aryl radical, an alkylaryl or arylalkyl radical having from 1 to 10, preferably from 1 to 4, carbon atoms in the alkyl part, and from 6 to 22, preferably from 6 to 10, carbon atoms in the aryl part, with the radicals also being able to be halogenated. Particular preference is given to $R^5$ and $R^6$ each being hydrogen, a cyclic, branched or unbranched $C_1$-$C_8$-alkyl radical, a $C_6$-$C_{10}$-aryl radical, an alkylaryl or arylalkyl radical having from 1 to 4 carbon atoms in the alkyl part and from 6 to 10 carbon atoms in the aryl part. Examples of particularly preferred radicals $R^5$ and $R^6$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, in particular methyl, phenyl or hydrogen, especially hydrogen.

The radicals $R^7$ may be identical or different and are each $C_1$-$C_4$-alkyl such as methyl, ethyl or tert-butyl, in particular methyl, $C_6$-$C_{10}$-aryl such as phenyl or naphthyl, in particular phenyl, alkylaryl or arylalkyl having from 1 to 4 carbon atoms in the alkyl part and from 6 to 10, preferably 6, carbon atoms in the aryl part.

The radicals $R^{10}$, $R^{11}$, $R^{12}$ and $R^{13}$ may be identical or different and are each hydrogen or a $C_1$-$C_{40}$ radical, for example a $C_1$-$C_{40}$-hydrocarbon radical, or $C_3$-$C_{40}$—Si($R^7$)$_3$, or two adjacent radicals $R^{10}$, $R^{11}$, $R^{12}$ and $R^{13}$ together with the two carbon atoms connecting them can form a cyclic ring system which may contain one or more, identical or different heteroatoms selected from the group consisting of the elements N, O, P, S and Si, preferably N, O or S, in place of carbon atoms. Preference is given to the radicals $R^{10}$, $R^{11}$, $R^{12}$ and $R^{13}$ each being hydrogen, a cyclic, branched or unbranched $C_1$-$C_{20}$, preferably $C_1$-$C_8$-alkyl radical, a $C_8$-$C_{22}$—, preferably $C_6$-$C_{10}$-aryl radical, an alkylaryl or arylalkyl radical having from 1 to 10, preferably from 1 to 4, carbon atoms in the alkyl part and 6 to 22, preferably from 6 to 10, carbon atoms in the aryl part, with the radicals also being able to be halogenated, or $C_3$-$C_{18}$—, preferably $C_3$-$C_8$—Si($R^7$)$_3$, or two adjacent radicals $R^{10}$, $R^{11}$, $R^{12}$ and $R^{13}$ together with the two carbon atoms connecting them forming a cyclic 4- to 8-membered, preferably 5- or 6-membered, in particular 6-membered, ring system which may in turn bear $C_1$-$C_{20}$ radicals. Particular preference is given to the radicals $R^{10}$, $R^{11}$, $R^{12}$ and $R^{13}$ being hydrogen, a cyclic, branched or unbranched $C_1$-$C_8$-alkyl radical, a $C_6$-$C_{10}$-aryl radical, an alkylaryl or arylalkyl radical having from 1 to 4 carbon atoms in the alkyl part and from 6 to 10 carbon atoms in the aryl part or trimethylsilyl or two adjacent radicals $R^{10}$, $R^{11}$, $R^{12}$ and $R^{13}$ together with the two carbon atoms connecting them forming a cyclic 5- or 6-membered ring system which may in turn bear cyclic, branched or un-branched $C_1$-$C_8$-alkyl radicals, $C_8$-$C_{10}$-aryl radicals, alkylaryl or arylalkyl radicals having from 1 to 4 carbon atoms in the alkyl part and from 6 to 10 carbon atoms in the aryl part or trimethysilyl radicals.

Examples of particularly preferred radicals $R^{10}$, $R^{11}$, $R^{12}$ and $R^{13}$ are methyl, ethyl, n-propyl, isopropyl, n-butyl, 1-butyl, s-butyl, t-butyl, n-pentyl, cyclopentyl, n-hexyl, cyclohexyl, n-heptyl, n-octyl, adamantyl, benzyl, triphenylmethyl, 1-1-diphenylethyl, 1-methyl-1-phenylethyl, 2-phenylethyl, phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, t-cyclohexylphenyl and p-trimethylsilylphenyl. Examples of particularly preferred ring systems formed from two adjacent radicals $R^{10}$, $R^{11}$, $R^{12}$ and $R^{13}$ together with the two carbon atoms connecting them are a phenyl ring, pyrridine ring or thiophene ring.

It is preferred that radicals $R^{10}$, $R^{11}$, $R^{12}$ and $R^{13}$ having the same indices are in each case identical.

It is preferred that the radical $R^{10}$ is not hydrogen and is a bulky radical such as a branched or cyclic $C_1$-$C_{10}$-alkyl radical, a $C_6$-$C_{10}$-aryl radical, an alkylaryl or arylalkyl radical having from 1 to 4 carbon atoms in the alkyl part and from 6 to 10 carbon atoms in the aryl part. Examples of particularly preferred radicals $R^{10}$ are isopropyl, t-butyl, cyclohexyl, adamantyl, triphenylmethyl, 1,1-diphenylethyl, 1-methyl-1-phenylethyl, phenyl, pentafluorophenyl, 3,5-di(tert-butyl)phenyl, 2,4,6-trimethylphenyl, 1-naphthyl, phenanthryl, p-tert-butylphenyl. An example of a particularly preferred ring system formed from the radicals $R^{10}$ and $R^{11}$ together with the two carbon atoms connecting them is a phenyl ring.

Illustrative examples of transition metal compounds which can be used as constituent of the catalyst systems of the present invention are, without implying any restriction of the scope of the invention:

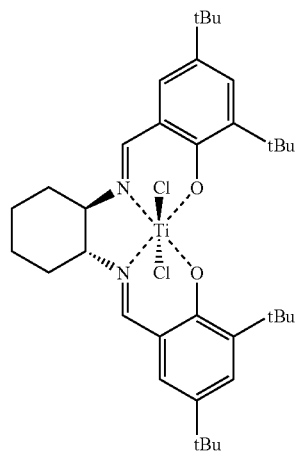

-continued

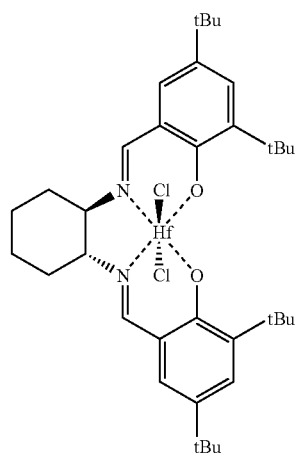

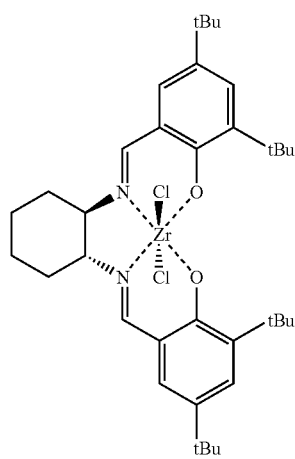

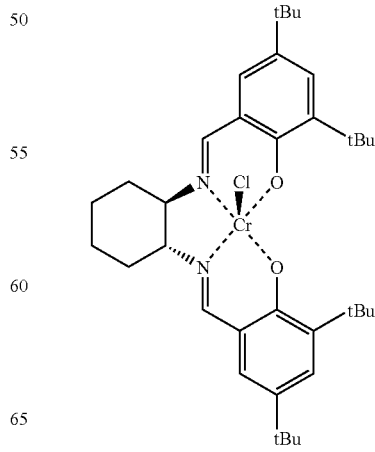

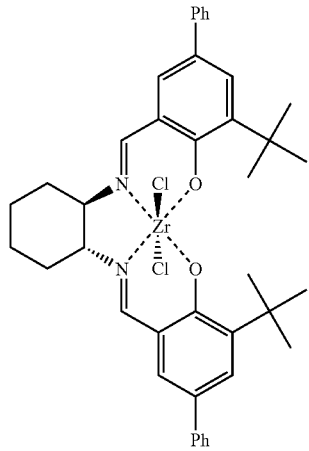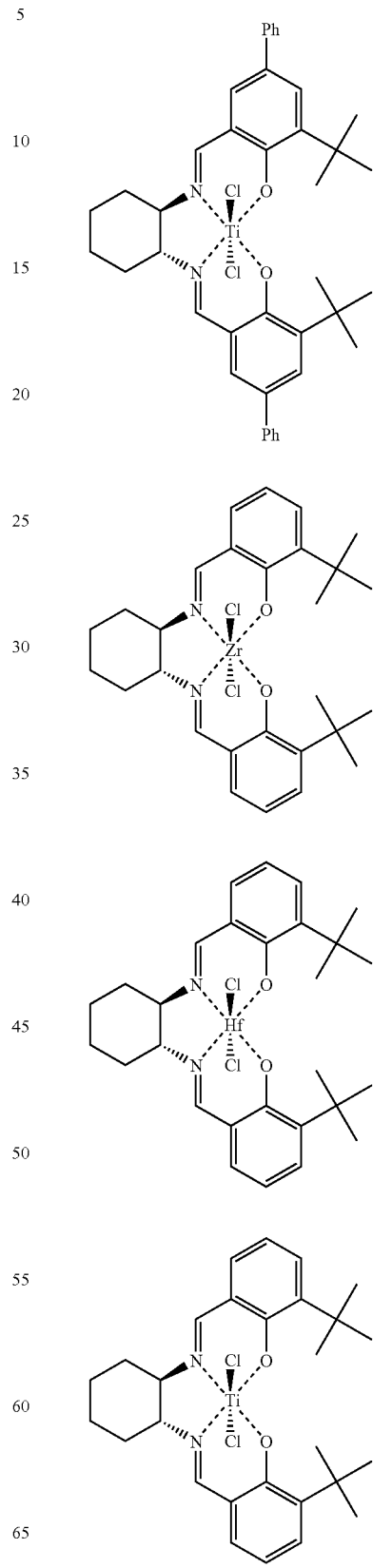

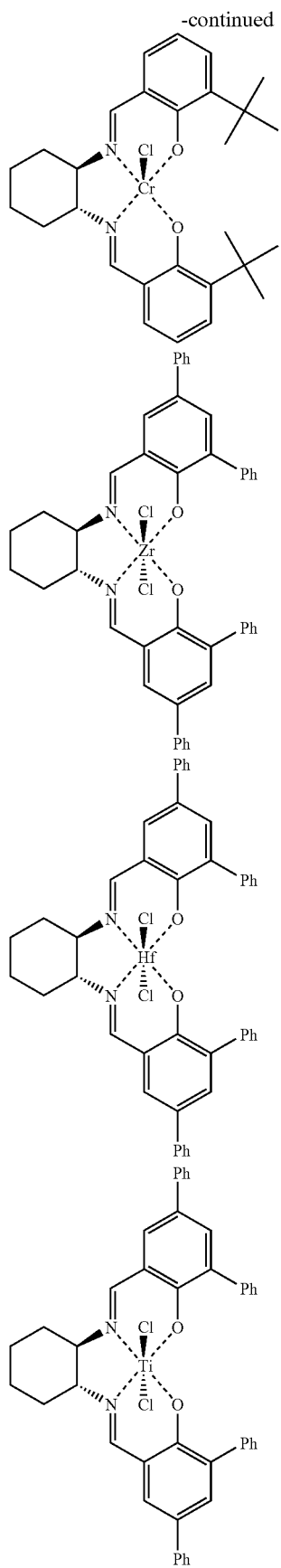
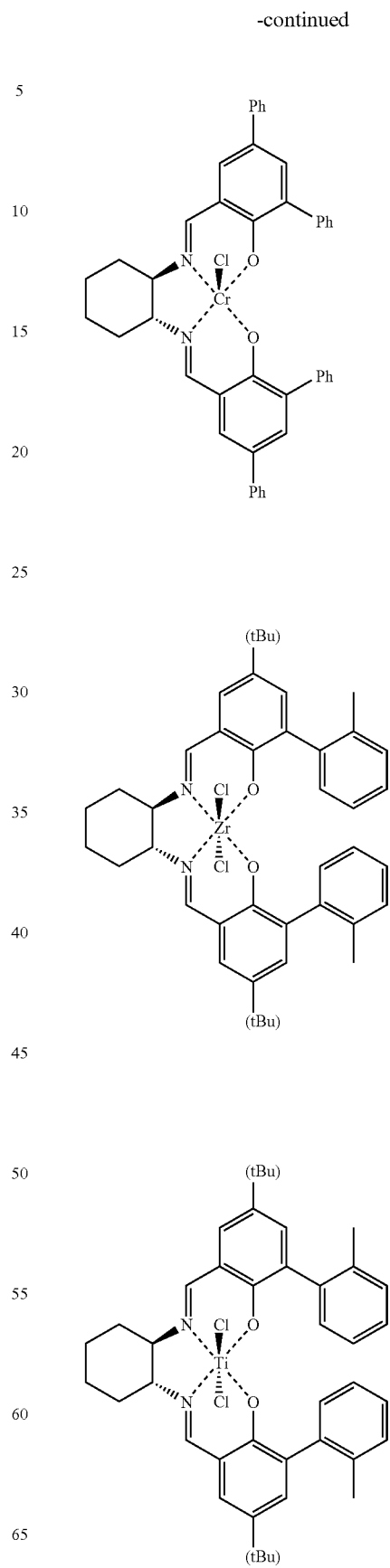

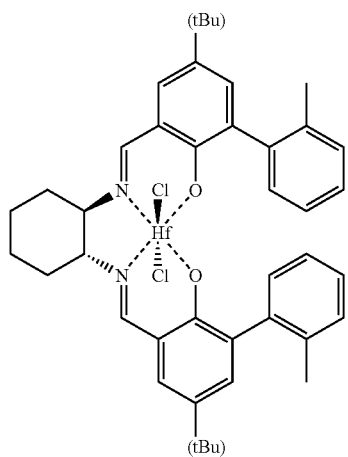
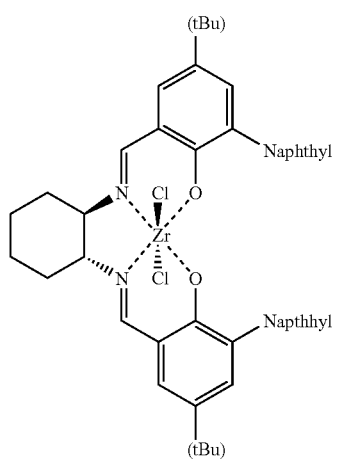
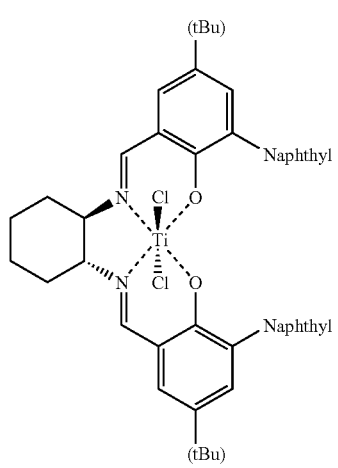
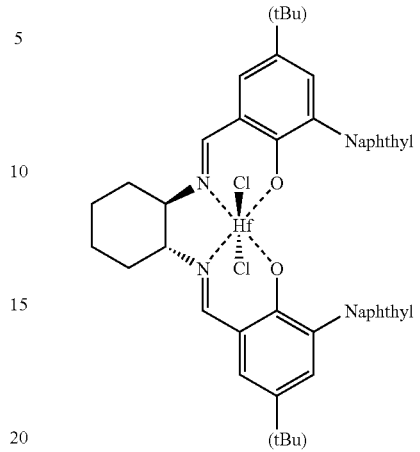
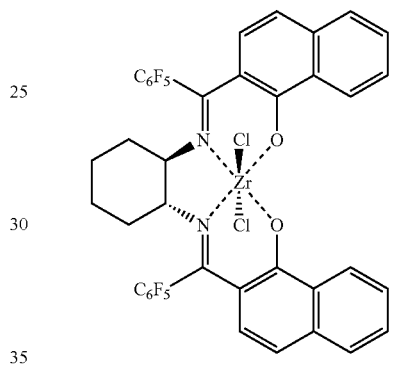
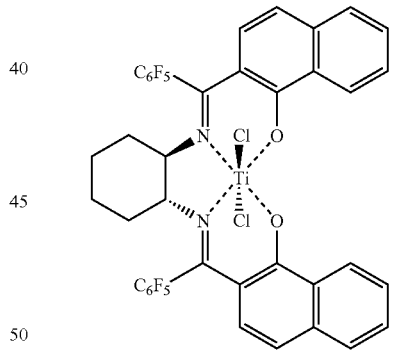
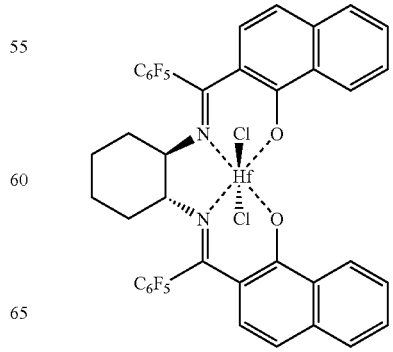

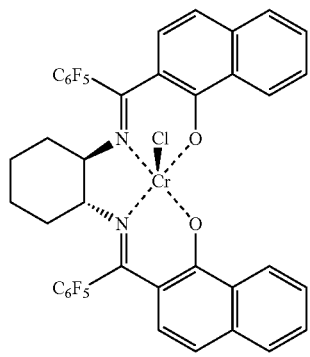
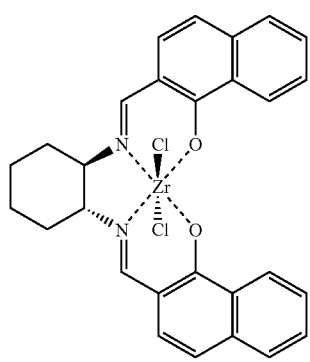
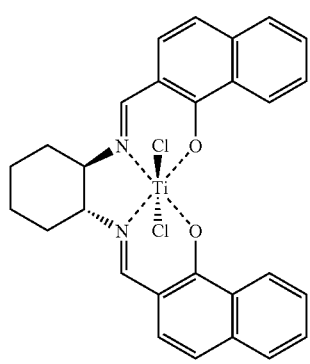
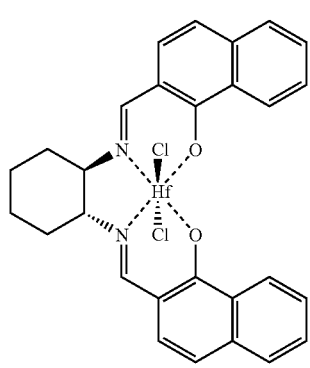
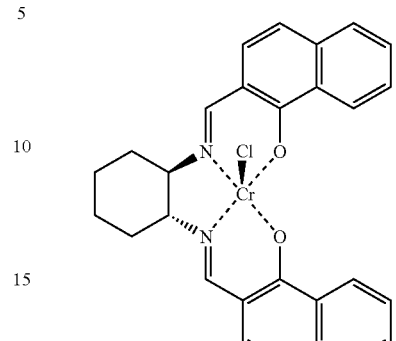
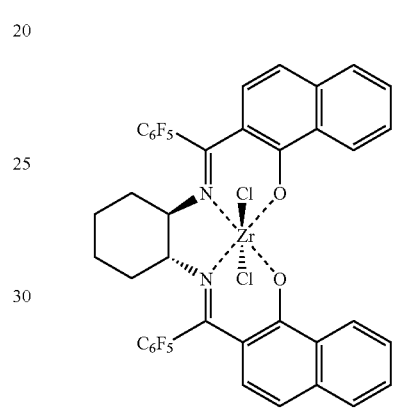
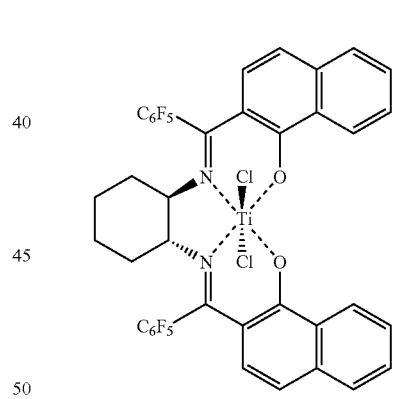
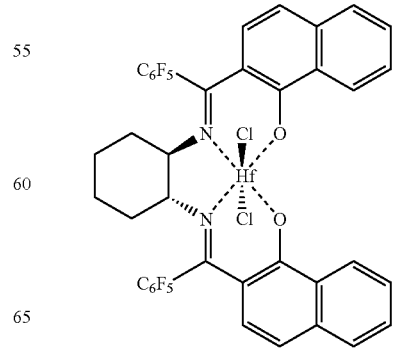

-continued
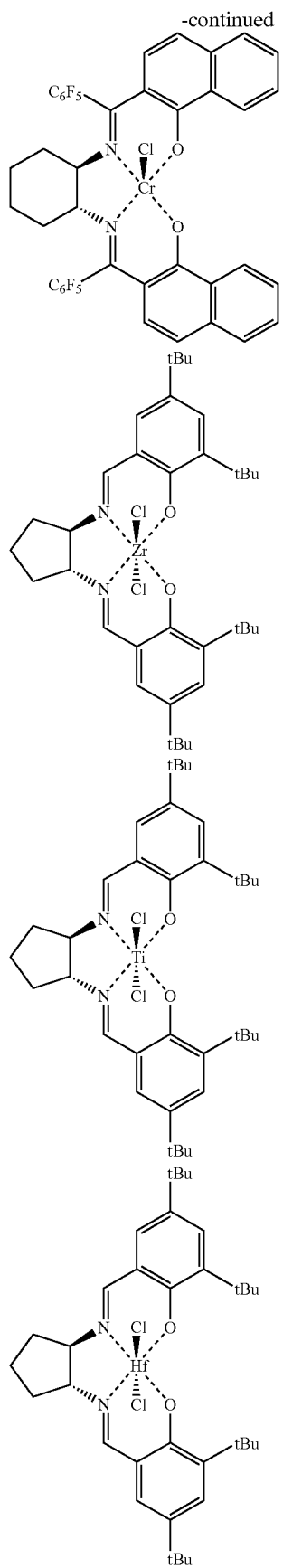
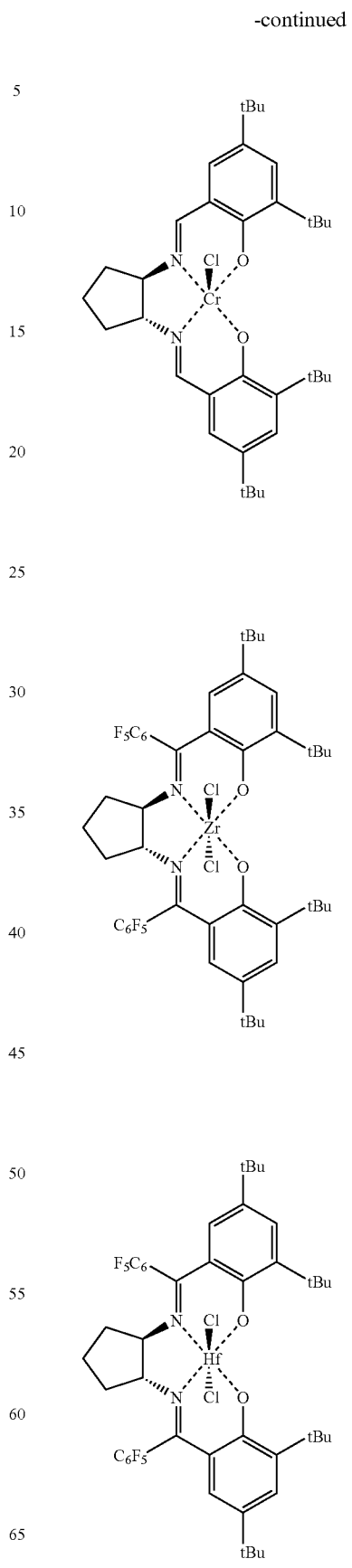

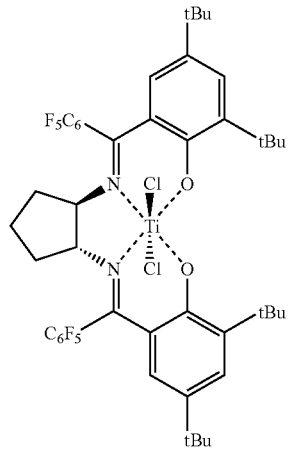
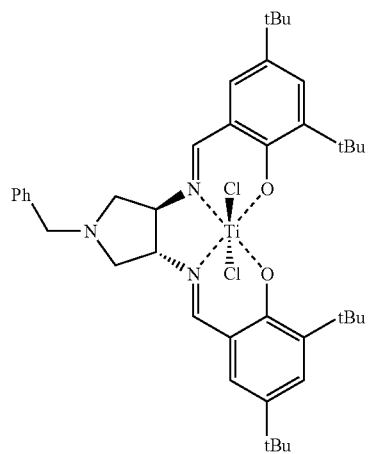
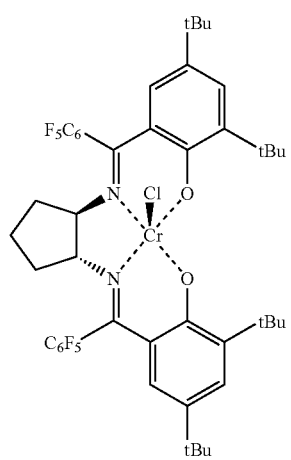
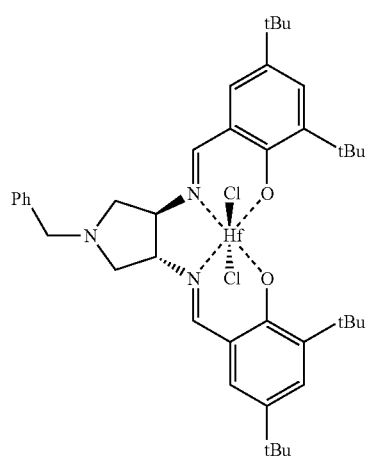
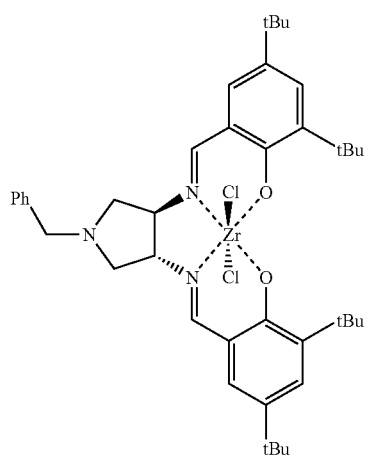
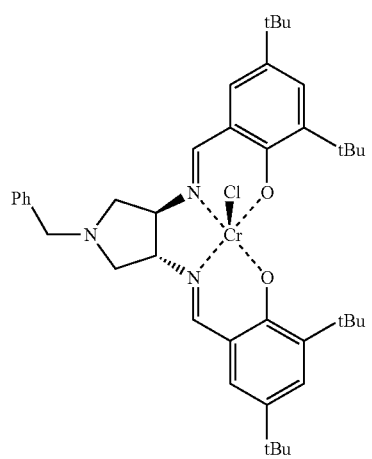

-continued
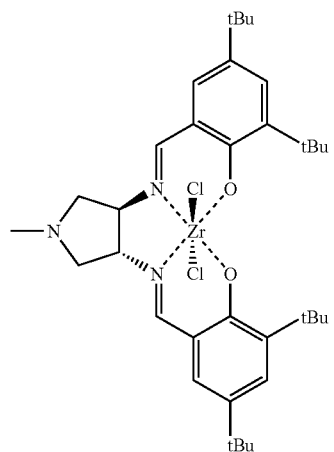
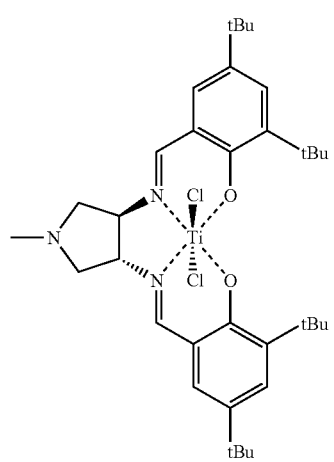
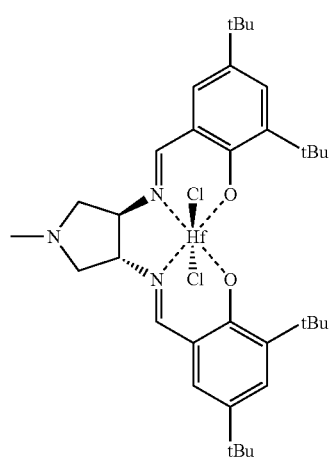
-continued
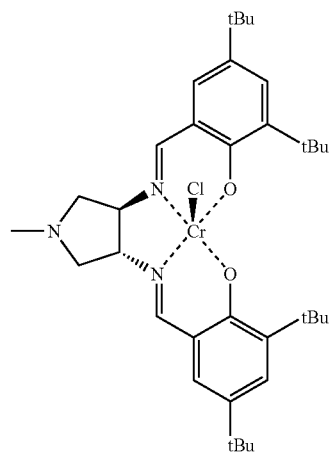
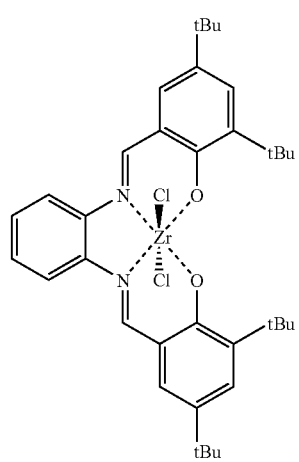
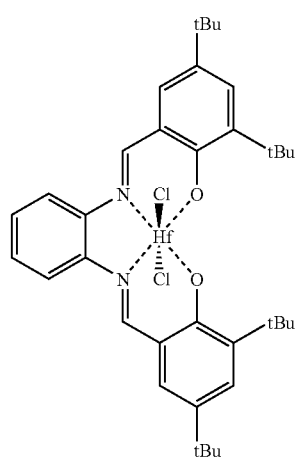

-continued
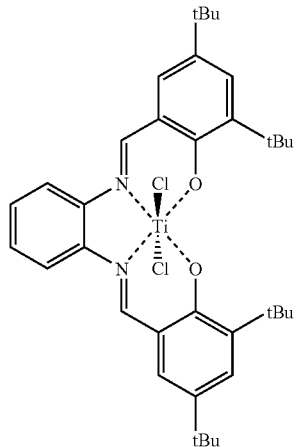
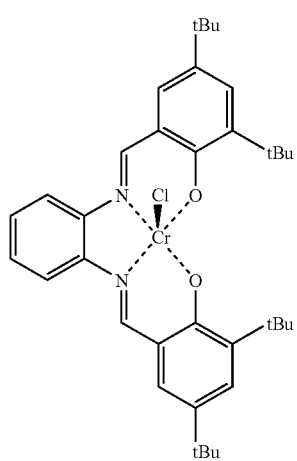
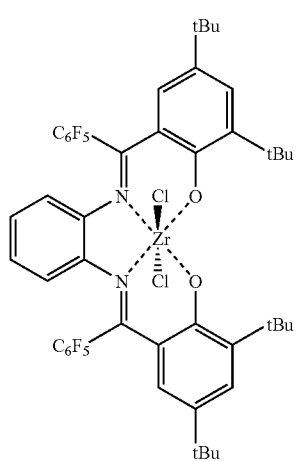
-continued
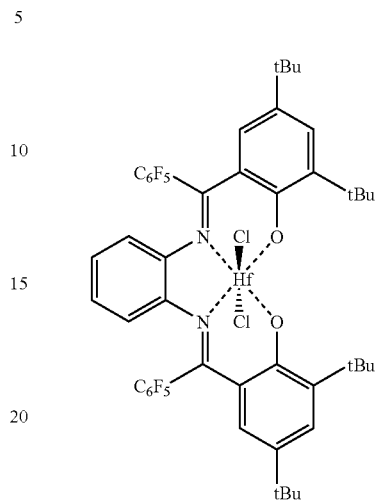
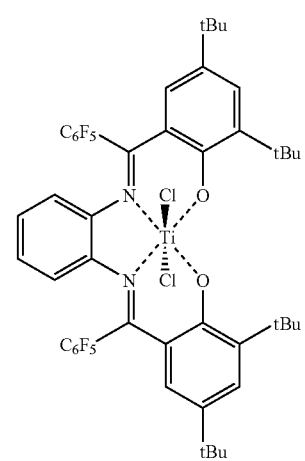

-continued
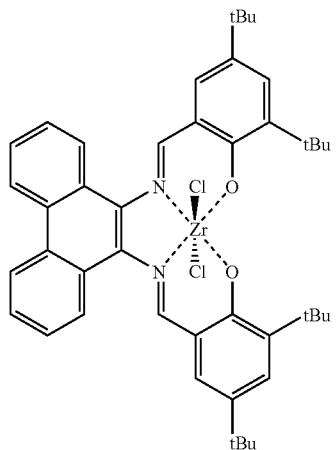
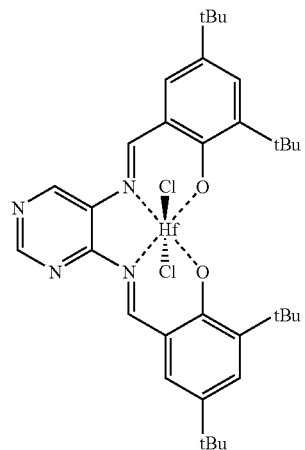
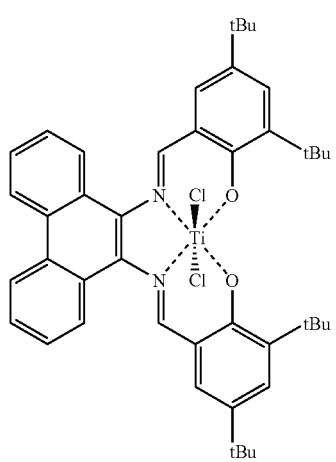
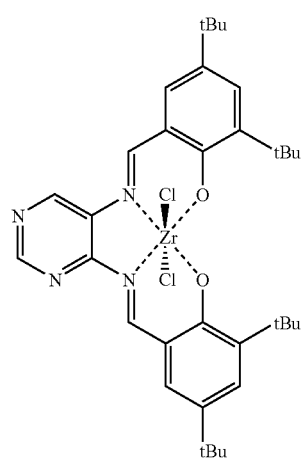
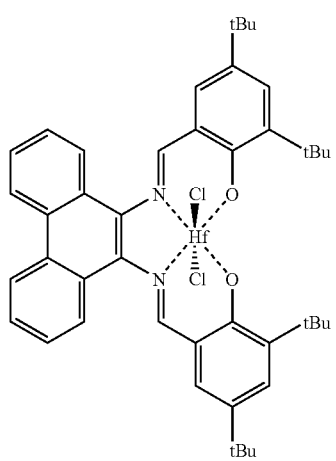
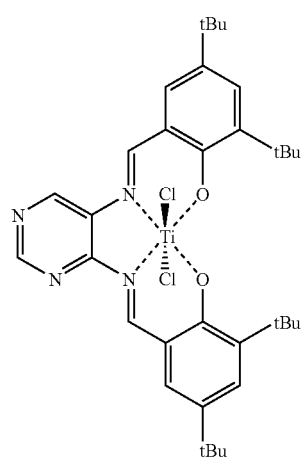

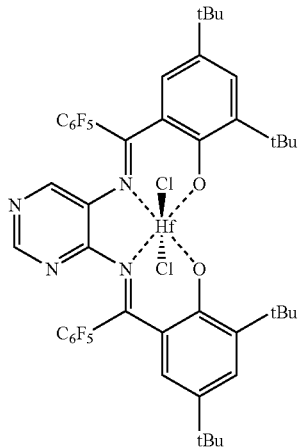
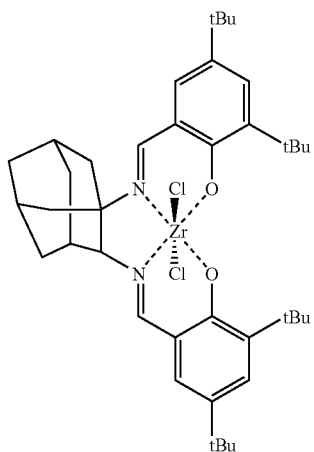
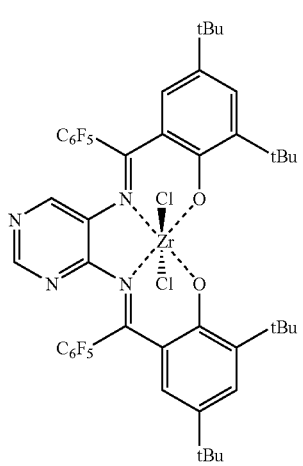
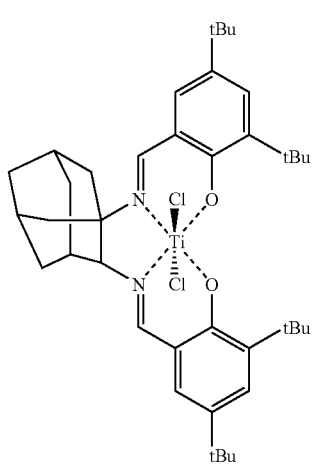
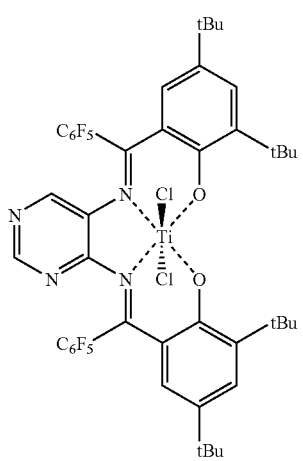
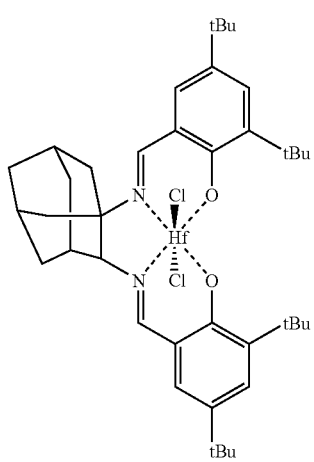

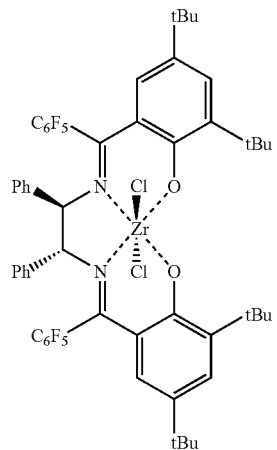
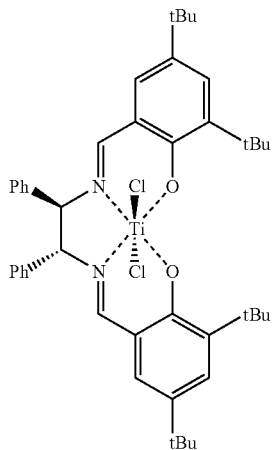
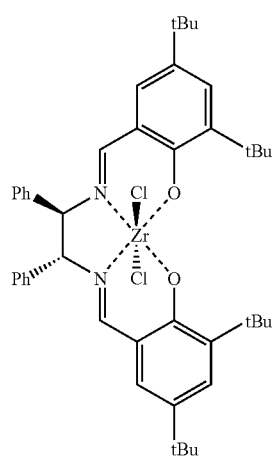
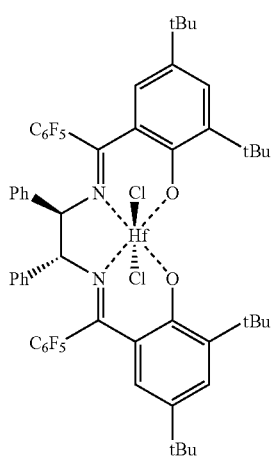
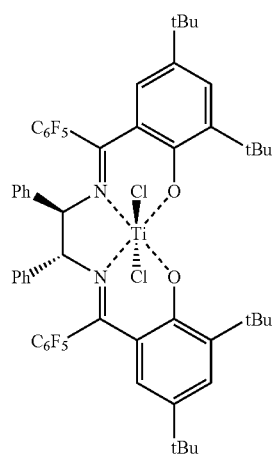
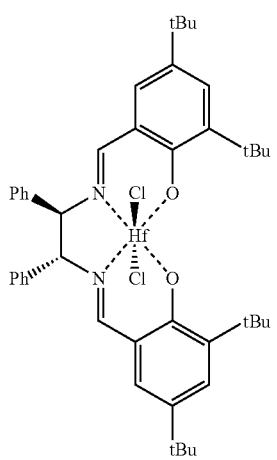

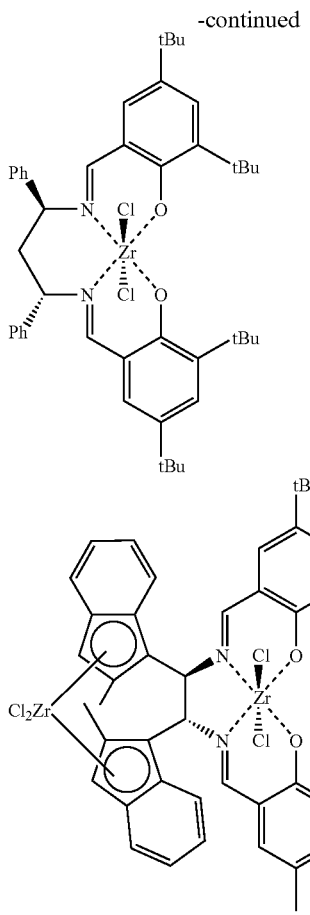

The preparation of the bridged chelating ligands and the chiral transition metal compounds prepared therefrom is known in principle from the literature and is described, for example, in WO 99/56699.

The cocatalyst which together with the chiral transition metal compound described in more detail above forms the novel, polymerization-active catalyst system is able to convert the chiral transition metal compound into a cation.

Suitable cation-forming compounds are, for example, aluminoxanes, strong uncharged Lewis acids, ionic compounds having a Lewis-acid cation or tonic compounds containing a Brönsted acid as cation. Preference is given to an aluminoxane as cocatalyst.

As aluminoxanes, it is possible, for example, to use the compounds described in WO 00131 090. Particularly useful compounds of this type are open-chain or cyclic aluminoxane compounds of the formula (II) or (III)

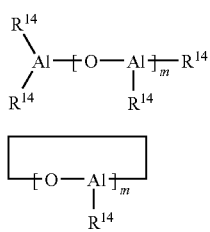

where
$R^{14}$ is a $C_1$-$C_4$-alkyl group, preferably a methyl or ethyl group, and m is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that m is to be regarded as a mean. The aluminoxane compounds can also be present in admixture with other metal alkyls, preferably aluminum alkyls.

Furthermore, it is also possible to use modified aluminoxanes in which some of the hydrocarbon radicals or hydrogen atoms have been replaced by alkoxy, aryloxy, siloxy or amide radicals in place of the aluminoxane compounds of the formula (II) or (III).

It has been found to be advantageous to use the chiral transition metal compound and the aluminoxane compounds in such amounts that the atomic ratio of aluminum from the aluminoxane compounds to the transition metal from the transition metal compound is in the range from 10:1 to 1000:1, preferably in the range from 20:1 to 500:1 and in particular in the range from 30:1 to 400:1.

As strong, uncharged Lewis acids, preference is given to compounds of the formula (IV)

$$M^2X^1X^2X^3 \qquad (IV)$$

where
$M^2$ is an element of group 13 of the Periodic Table of the Elements, in particular B, Al or Ga, preferably B,
$X^1$, $X^2$ and $X^3$ are each, independently of one another, hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are mentioned in WO 00/31090.

Particular preference is given to compounds of the formula (IV) in which $X^1$, $X^2$ and $X^3$ are identical, preferably tris(pentafluorophenyl)borane.

Strong uncharged Lewis acids which are suitable as cation-forming compounds also include the reaction products of the reaction of a boronic acid with two equivalents of a trialkyl aluminum or the reaction products of the reaction of a trialkyl aluminum with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the formula (V)

$$[(Y^{a+})Q_1Q_2 \ldots Q_z]^{d+} \qquad (V)$$

where
Y is an element of groups 1 to 16 of the Periodic Table of the Elements,
$Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 5 to 20 carbon atoms in the aryl radical and from 1 to 28 carbon atoms in the alkyl radical, $C_3$-$C_{10}$-cycloalkyl, which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is an integer from 0 to 5, and d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have non-coordinating counterions, in particular borane compounds as are mentioned in WO 91/09882, preferably tetrakis(pentafluorophenyl)borate.

Salts having non-coordinating anions can also be prepared by combining a borane or aluminum compound, e.g. an aluminum alkyl, with a second compound which can react to link two or more borane or aluminum atoms, e.g. water, and a third compound which forms an ionizing ionic compound with the borane or aluminum compound, e.g. triphenylchloromethane. A fourth compound which likewise reacts with the borane or aluminum compound. e.g. pentafluorophenol, can additionally be added.

Ionic compounds containing Brönsted acids as cations preferably likewise have non-coordinating counterions. As Brönsted acids, particular preference is given to protonated amine or aniline derivatives. Preferred cations are N,N-demethylanilinium, N,N-diemethylcyclohexylammonium and N,N-dimethylbenzylammonium and also derivatives of the latter two.

Preferred ionic compounds as cation-forming compounds are, in particular, N,N-dimethylanilinium tetrakis(pentafluorophenyl)borate, N,N-dimethylcyclohexylammonium tetrakis(pentafluorophenyl)borate and N,N-dimethylbenzylammonium tetrakis(pentafluorophenyl)borate.

It is also possible for two or more borate anions to be joined to one another, as in the dianion $[(C_8F_5)_2B-C_6F_4-B(C_6F_5)_2]^{2-}$, or the borate anion can be bound via a bridge having a suitable functional group to the surface of a support particle.

Further suitable cation-forming compounds are listed in WO 00/131090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, based on the chiral transition metal compound.

Suitable cation-forming compounds also include borane-aluminum compounds such as di[bis(pentafluorophenyl)boroxy]methylalene. Appropriate borane-aluminum compounds are disclosed, for example, in WO 99/06414.

It is also possible to use mixtures of all the abovementioned cation-forming compounds. Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the transition metal compound and the cation-forming compounds in a solvent, preferably an aromatic hydrocarbon having from 6 to 20 carbon atoms, in particular xylenes and toluene.

The catalyst system of the present invention can further comprise a metal compound of the formula (VI),

$$M^3(R^{15})_r(R^{16})_s(R^{17})_t \qquad (VI)$$

where $M^3$ is an alkali metal, an alkaline earth metal or a metal of group 13 of the Periodic Table of the Elements, i.e. borane, aluminum, gallium, indium or thallium, $R^{15}$ is hydrogen, $C_1$-$C_{10}$-alkyl, $C_8$-$C_{15}$-aryl, alkylaryl or arylalkyl each having from 1 to 10 carbon atoms in the alkyl part and from 6 to 20 carbon atoms in the aryl part, $R^{16}$ and $R^{17}$ are identical or different and are each hydrogen, halogen, $C_1$-$C_{10}$-alkyl, $C_8$-$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3, and s and t are integers from 0 to 2, with the sum r+s+t corresponding to the valence of $M^3$, where the metal compound of the formula (VI) is usually not identical to the cation-forming compound. It is also possible to use mixtures of various metal compounds of the formula (VI).

Among the metal compounds of the formula (VI), preference is given to those in which $M^3$ is lithium, magnesium or aluminum and $R^{16}$ and $R^{17}$ are each $C_1$-$C_{10}$-alkyl.

Particularly preferred metal compounds of the formula (VI) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

If a metal compound of the formula (VI) is used, it is preferably present in the catalyst system of the present invention in such an amount that the molar ratio of $M^3$ from formula (VI) to transition metal from the chiral transition metal compound is from 800:1 to 1:1, in particular from 200:1 to 2:1.

The catalyst system of the present invention particularly preferably further comprises a support.

To obtain such a supported catalyst system, the unsupported catalyst system can be reacted with a support. In principle, the support, the chiral transition metal compound and the cocatalyst can be combined in any order. The chiral transition metal compound and the cocatalyst can be immobilized independently of one another or simultaneously. After each individual process step, the solid can be washed with suitably inert solvents, e.g. aliphatic or aromatic hydrocarbons.

Supports used are preferably finely divided supports which can be any organic or inorganic, inert solid. In particular, the support is a porous solid such as talc, a sheet silicate, an inorganic oxide or a finely divided polymer powder (e.g. polyolefin).

Suitable inorganic oxides may be found among oxides of elements of groups 2, 3, 4, 6, 13, 14, 15 and 16 of the Periodic Table of the Elements. Examples of oxides preferred as supports include silicone dioxide, aluminum oxide and mixed oxides of the elements calcium, aluminum, silicone, magnesium or titanium and corresponding oxide mixtures. Other inorganic oxides which can be used alone or in combination with the abovementioned preferred oxidic supports are, for example, MgO, $ZrO_2$, $TiO_2$ or $B_2O_3$. An example of a preferred mixed oxide is calcite hydrotalcite.

The support materials used preferably have a specific surface area in the range from 10 to 1000 $m^2/g$, a pore volume in the range from 0.1 to 5 ml/g and a mean particle size of from 1 to 500 μm.

Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 100 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or under a blanket of inert gas (e.g. nitrogen), or the inorganic support can be calcined at from 200 to 1000° C. to obtain, if appropriate, the desired structure of the solid and/or to set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090. The inorganic support material can also be chemically modified. For example, treatment of silica gel with $(NH_4)_sSiF_6$ leads to fluorination of the silica gel surface or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrenes, via whose functional groups, for example ammonium or hydroxy groups, at least one of the catalyst components can be immobilized.

In a preferred embodiment of the preparation of the supported catalyst system of the present invention, at least one chiral transition metal compound is brought into contact with at least one cocatalyst as cation-forming compound in a suitable solvent, preferably giving a soluble reaction product, an adduct or a mixture.

The preparation obtained in this way is then mixed with the dehydrated or passivated support material, the solvent is removed and the resulting supported transition metal compound catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277.

A further preferred embodiment comprises firstly applying the cation-forming compound to the support component and subsequently bringing this supported cation-forming compound into contact with the chiral transition metal compound.

Combinations obtained by combining the following components are therefore likewise of importance as cocatalyst systems:

1st component: at least one defined borane or aluminum compound,
2nd component: at least one uncharged compound which has at least one acidic hydrogen atom,
3rd component at least one support, preferably an inorganic oxidic support, and optionally, as 4th component, a base, preferably an organic nitrogen-containing base, for example an amine, an aniline derivative or a nitrogen heterocycle.

The borane or aluminum compounds used in the preparation of the supported cocatalysts are preferably compounds of the formula (VII)

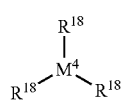

(VII)

where
$R^{18}$ are identical or different and are each hydrogen, halogen, $C_1$-$C_{20}$-alkyl, $C_1$-$C_{20}$-haloalkyl, $C_1$-$C_{10}$-alkoxy, $C_8$-$C_{20}$-aryl, $C_8$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl or an $OSiR^{19}{}_3$ group, where
$R^{19}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_8$-alkyl or $C_7$-$C_{20}$-arylalkyl, and
$M^4$ is borane or aluminum, preferably aluminum.

Particularly preferred compounds of the formula (VII) are trimethylaluminum, trimethylaluminum and tri-isobutylaluminum.

The uncharged compounds which have at least one acidic hydrogen atom and can react with compounds of the formula (VII) are preferably compounds of the formulae (VII), (IX) and (X).

  (VIII)

  (IX)

  (X)

where
$R^{20}$ are identical or different and are each hydrogen, halogen, a boron-free $C_1$-$C_{40}$ group such as $C_1$-$C_{20}$-alkyl, $C_1$-$C_{20}$-haloalky, $C_1$-$C_{10}$-alkoxy, $C_8$-$C_{20}$-aryl, $C_8$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, an $Si(R^{22})_3$ group or a $CH(SiR^{22}{}_s)_2$ group, where is a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl; $C_7$-$C_{40}$-alkylaryl, $C_7$-$C_{40}$-haloalkylaryl, and
$R^{21}$ is a divalent $C_1$-$C_{40}$ group such as $C_1$-$C_{20}$-alkylene, $C_1$-$C_{20}$-haloalkylene, $C_5$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene,
D is an element of group 16 of the Periodic Table of the Elements or an $NR^{23}$ group, where $R^{23}$ is hydrogen or a $C_1$-$C_{20}$-hydrocarbon radical such as $C_1$l-$C_{20}$-alkyl or $C_8$-$C_{20}$-aryl, preferably oxygen, and
h is 1 or 2.

Suitable compounds of the formula (VIII) include water, alcohols, phenol derivatives, thiophenol derivatives or aniline derivatives, with halogenated and in particular perfluorinated alcohols and phenols being of particular importance. Examples of particularly useful compounds are pentafluorophenol, 1,1-bis(pentafluorophenyl)methanol and 4hydroxy-2,2',3,3',4,4',5,5',6,6'-nonafluorobiphenyl.

Suitable compounds of the formula (IX) include boronic acids and borinic acids; particular mention may be made of borinic acids having perfluorinated aryl radicals, for example $(C_6F_5)_2BOH$. Suitable compounds of the formula (X) include dihydroxy compounds in which the divalent carbon-containing group is preferably halogenated and in particular perfluorinated. An example of such a compound is 4,4'-dihydroxy-2,2',3,3',5,5',6,6'-octafluorobiphenyl hydrate.

Examples of combinations of compounds of the formula (VII) with compounds of the formula (VIII) or (X) are trimethylaluminum/pentafluorophenol, trimethylaluminum/1-bis (pentafluorophenyl)methanol, trimethylaluminum/4-hydroxy-2,2',3,3',4',5,5',6,6'-nonafluorobiphenyl, triethylaluminum/pentafluorophenol, tri-isobutylaluminum/ pentafluorophenol and triethylaluminum/4,4'-dihydroxy2,2', 3,3',5,5',6,6'-octafluorobiphenyl hydrate, with, for example, reaction products of the following type being able to be formed.

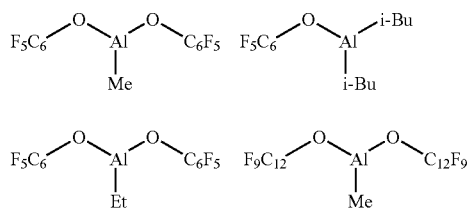

Examples of reaction products from the reaction of at least one compound of the formula (VII) with at least one compound of the formula (IX) are:

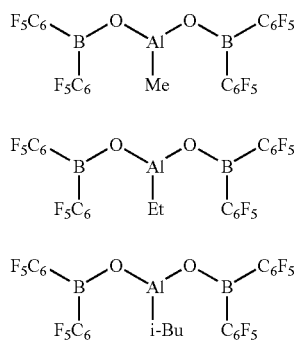

The way in which the components are combined is in principle immaterial.

In one possible method, the reaction products of the reaction of at least one compound of the formula (VII) with at least one compound of the formula (VIII), (IX) or (X) and optionally the organic nitrogen base are combined with an organometallic compound of the formula (II), (III), (IV) and/or (VI) and then with the support to form the supported cocatalyst system.

In a preferred variant, the 1st component, e.g. compounds of the formula (VII), and the 2nd component, e.g. compounds of the formula (VIII), (IX) or (X), and also a support as 3rd component and a base as 4th component are combined separately and subsequently reacted with one another, preferably in an inert solvent or suspension medium. The supported cocatalyst formed can then be freed of the inert solvent or suspension medium before being reacted with the chiral transition metal compound used according to the present invention and, if appropriate, a metal compound of the formula (VI) to give the catalyst system of the present invention.

Furthermore, it is also possible firstly to prepolymerize the catalyst solid according to the present invention with α-olefins, preferably linear $C_2$-$C_{10}$-1-alkenes and in particular ethylene or propylene and then to use the resulting prepolymerized catalyst solid in the actual polymerization. The molar ratio of catalyst solid used in the prepolymerization to monomer polymerized onto it is usually in the range from 1:0.1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or an oil can be added as additive during or after the preparation of the supported catalyst system of the present invention. The molar ratio of additives to chiral transition metal compound is in this case usually from 1-1000 to 1000:1, preferably from 1:5 to 20:1.

The novel catalyst systems based on the above-described chiral transition metal compounds give isotactic polyolefins, in particular isotactic polypropylene, having a higher melting point than do the previously known catalyst systems.

The invention further provides for the use of a novel catalyst system as described above for preparing polyolefins and provides processes for preparing polyolefins by polymerization or copolymerization of at least one olefin, in particular propylene in the presence of a novel catalyst system as described above.

In general, the catalyst system of the present invention is used together with a further metal compound of the formula (VI), which may be different from the metal compound or compounds of the formula (VI) used in the preparation of the catalyst system of the present invention for the polymerization or copolymerization of olefins. The further metal compound is generally added to the monomer or to the suspension medium and serves to free the monomer of substances which could adversely affect the catalyst activity. It is also possible to add one or more further cation-containing compounds to the catalyst system of the present invention during the polymerization process.

The olefins can be functionalized, olefinically unsaturated compounds such as ester or amide derivatives of acrylic or methacrylic acid, for example acrylates, methacrylates or acrylonitrile, or can be nonpolar olefinic compounds, including aryl-substituted α-olefins.

Preference is given to polymerizing olefins of the formula $R^m$—CH=CH—$R^n$, where $R^m$ and $R^n$ are identical or different and are each hydrogen or a hydrocarbon radical having from 1 to 20 carbon atoms, in particular from 1 to 10 carbon atoms, or $R^m$ and $R^n$ together with the atoms connecting them can form one or more rings.

Examples of such olefins are 1-olefins having from 2 to 40, preferably from 2 to 10, carbon atoms, for example ethylene, propylene, 1-butene, 1-pentene, 1-hexene, 1-heptene, 1-octene, 1-decene or 4-methyl-1-pentene, or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene. Preference is given to, propylene, 1-butene, 1-hexene or 4-methyl-1-pentene, in particular propylene.

The catalyst system of the present invention is particularly preferably used for homopolymerizing propylene or ethylene, in particular propylene, or copolymerizing ethylene with $C_3$-$C_8$-α-olefins such as propylene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene, or very particularly preferably copolymerizing propylene with ethylene and/or 1-butene. Examples of such copolymers are propyleneethylene, propylene/1-butene, ethylene/1-butene, ethylene/1-hexene, ethylene/1-octene copolymers, ethylene/propylene/ethylidenenorbornene or ethylene/propylene/1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvent or suspension medium, it is possible to use inert hydrocarbons, for example isobutane, or else the monomers themselves.

The polymerization can be carried out at from −60 to 300° C. at pressures in the range from 0.5 to 3000 bar. Preference is given to temperatures in the range from 50 to 200° C., in particular from 60 to 100° C., and pressures in the range from 5 to 100 bar, in particular from 15 to 70 bar. The mean residence times are usually from 0.5 to 5 hours, preferably from 0.5 to 3 hours. As molar mass regulator and/or to increase the activity, hydrogen can be employed in the polymerization. It is also possible to use customary additives such as antistatics. The catalyst system of the present invention can be used directly for the polymerization, i.e. it is added in pure form into the polymerization system, or it is admixed with inert components such as paraffins, oils or waxes to improve meterability.

The catalyst systems of the present invention are very particularly useful for preparing propylene homopolymers having high melting points.

The invention further provides for the use of a chiral transition metal compound of the formula (Ib) or one of its enantiomers of the formula (Ib*) for preparing a catalyst system for the polymerization of olefins, in particular for homo- or copolymerization of propylene,

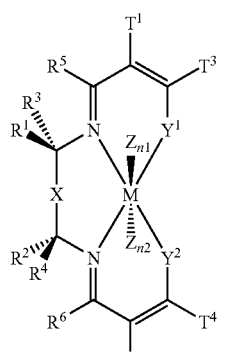

(Ib)

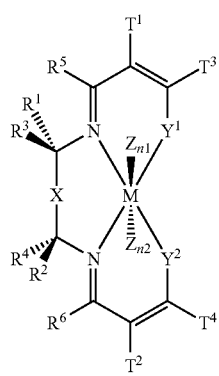

(Ib*)

where the variables are as defined for the formulae (I) and (I*).

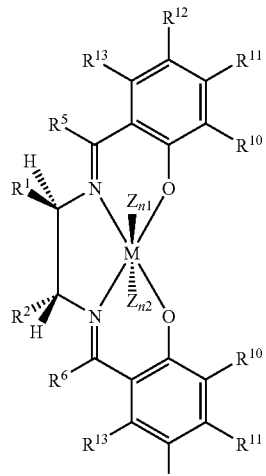

(Ic)

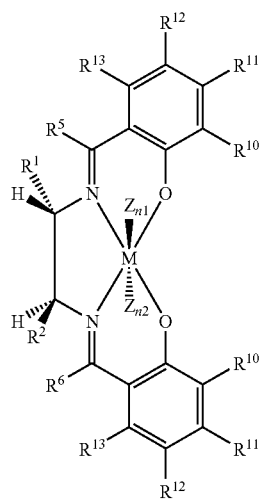

(Ic*)

where the variables are as defined for the formulae (Ia) and (Ia*) is particularly preferred for the preparation of a catalyst system.

The invention further provides chiral transition metal compounds of the formula (Ib) or (Ib*) in which M is zirconium or hafnium, in particular zirconium.

The invention additionally provides a process for preparing a catalyst system for olefin polymerization, which comprises reacting at least one transition metal compound of the formula (Ib) or (Ib*) with at least one cation-forming compound, and also a process for preparing isotactic polyolefins by polymerization of at least one α-olefin, in particular propylene in the presence of a catalyst system prepared by the process just mentioned.

The invention further provides the polyolefins obtainable by one of the abovementioned polymerization processes, in particular homopolymers and copolymers of propylene, and also provides polyolefin compositions which comprise polyolefins obtainable using the catalyst systems of the present invention.

The isotactic polypropylenes which can be prepared by the process of the present invention have a viscosity number (or index of viscosity, I.V.) greater than 1, a melting point ($T_m$) greater than 158° C., preferably greater than 160° C., in particular greater than 163° C., an isotacticity determined by pentad analysis of the $^{13}$C-NMR spectrum of the polymer samples of greater than 98%, in particular greater than 99%, a frequency of reverse insertions determined by pentad analysis of the $^{13}$C-NMR spectrum of the polymer samples of less than 0.3%, in particular less than 0.25%, and a polydispersity Q=Mw/Mn of less than 3, in particular less than 2.5.

The polymers prepared by the process of the present invention and polyolefin compositions in which they are present are particularly useful for producing films, fibers and moldings.

The invention further provides films, fibers and moldings produced from the above-described polyolefin compositions.

The invention is illustrated by the following nonlimiting examples.

EXAMPLES

General Procedures

Synthesis and handling of the organic metal compounds and the catalysts were carried out in the absence of air and moisture under argon (Glove box and Schlenk technique). All solvents used were purged with argon and dried over molecular sieves before use.

(S,S)-(+)-N,N'-bis(3,5-di-tert-butylsalicylidene)-1,2-diaminocyclohexane, (R,R)-(−)-N,N'-bis(3,5-di-tert-butylsalicylidene)-1,2-diaminocyclohexane and (S,S)-(+)N,N'-bis(3, 5-di-tert-butylsalicylidene)-1,2-diaminocyclohexanechromium(III)chloride were commercially available. The preparation of supported catalyst systems was carried out using a silica of the type XPO 2107 from Grace dried at 180° C. under reduced pressure for is hours as silica gel.

Determination of the Melting Point:

The melting point $T_m$ was determined by means of a DSC measurement in accordance with ISO standard 3146 using a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the curve of enthalpy versus temperature measured in the second heating phase displayed its maximum.

Gel Permeation Chromatography:

Gel permeation chromatography (GPC) was carried out at 145° C. in 1,2,4-trichlorobenzene using a Waters 150 C GPC apparatus The data were evaluated using the software WinGPC from HS-Entwicklungsgesellschaft für wissenschaftliche Hard- und Software mbH. Oberhilbersheim. The columns were calibrated by means of polypropylene standards having molar masses ranging from 100 to $10^7$ g/mol. Mass average molar masses ($M_w$) and number average molar masses ($M_n$) of the polymers were determined. The Q value is the ratio of mass average ($M_w$) to number average ($M_n$).

Determination of the Viscosity Number (I.V.):

The viscosity number was determined in an Ubbelohde viscometer PVS 1 provided with an S 5 measuring head (both from Lauda) in decalin at 135° C. For the sample preparation, 20 mg of polymer were dissolved in 20 ml of decalin at 135° C. over a period of 2 hours. 15 ml of the solution were introduced into the viscometer and the instrument carried out a minimum of 3 running-out times measurements until a consistent result was obtained. From the running-out times, the I.V. was determined via the equation I.V.=(t/$t_o$−1)*1/c, where t: mean of the running-out time of the solution, $t_o$: mean of the running-out time of the solvent, c: concentration of the solution in g/ml.

Example 1

Synthesis of (S,S)-(+)-N,N'-bis(3,5-di-tert-butylsalicylidene)-1,2-diaminocyclohexane-titanium(IV) dichloride (1)

1.4 ml of a solution of n-butyllithium in hexane (3.6 mmol. 2.5M) was slowly added at room temperature to a solution of 1 g (1.8 mmol) of (S,S)-(+)-N,N'-bis(3,5-di-tert-butylsalicylidene)-1,2-diaminocyclohexane in 70 ml of diethyl ether. The yellow solution was stirred at room temperature for 1.5 hours and subsequently admixed with 0.34 g (1.8 mmol) of TiCl$_4$. The reaction mixture was stirred at room temperature for 18 hours, subsequently filtered and the solvent was removed in an oil pump vacuum. This gave 0.85 g of (1) as a red, free-flowing powder.

Example 2

Synthesis of (S,S-(+)-N,N'-bis(3,5-di-tert-butylsalicylidene)-1,2-diaminocyclohexanezirconium(IV) dichloride (2)

6.8 ml of a solution of n-butyllithium in hexane (10.9 mmol, 1.6M in hexane) were slowly added at room temperature to a solution of 2.94 g (5.38 mmol) of (S,S)-(+)-N,N'-bis-(3,5-di-tert-butylsalicylidene)-1,2-diaminocyclohexane in 100 ml of diethyl ether and the reaction mixture was stirred for 4 hours. 1.24 g (5.34 mmol) of ZrCl$_4$ were subsequently added a little at a time and the reaction mixture was stirred overnight. The solvents were subsequently removed in an oil pump vacuum, the solid was taken up in dichloromethane, filtered and dichloromethane was removed from the filtrate in an oil pump vacuum. This gave 4.06 g of (2) as a bright yellow, free-flowing powder.

Example 3

Synthesis of (R,R)-(−)-N,N'-bis(3,5-di-tert-butylsalicylidene)-1,2-diaminocyclohexanezirconium(IV) dichloride (3)

Using a method analogous to example 2, a solution of 3.3 g (6.04 mmol) of (R,R)-(−)-N,N'-bis(3,5-di-tert-butylsalicylidene)-1,2-diaminocyclohexane in 100 ml of diethyl ether was reacted with 7.55 ml of a solution of n-butyllithium in hexane (12.08 mmol, 1.6M). 1.4 g (6.04 mmol) of ZrCl$_4$ were subsequently added. Work-up by a method analogous to example 2 gave 4.77 g of (3) as a bright yellow, free-flowing powder. Crystals were obtained from a saturated solution of (3) in methylene chloride.

Figure 1B:
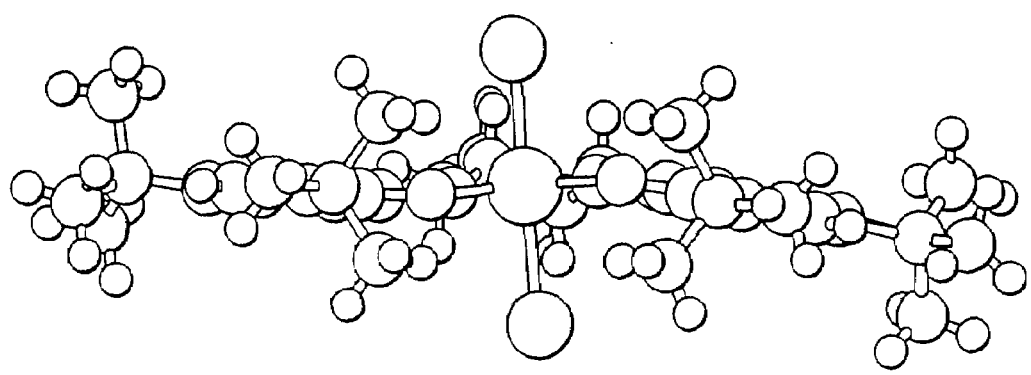

X-ray crystal structure analysis: FIGS. 1a and 1b show the structure of the compound (3) from different perspectives.

Example 4

Homopolymerization of Propene 4 ml of a solution of triisobutyl aluminum in hexane (4 mmol, 1M) were placed in a 1l reactor. 250 g of propylene were introduced at 30° C. and the contents of the reactor were heated to 50° C. A catalyst solution prepared by combining 10 mg of the titanium compound (1) (15.1 μmol) from example 1 with 2.5 ml of a solution of methylaluminoxane in toluene (3.95 mmol, 10% by weight) and subsequently allowing the mixture to react for 15 minutes was introduced into the reactor together with 50 g of propylene which had a temperature of 80° C. The contents of the reactor were stirred at 50° C. for 0.5 hour and the polymerization reaction was stopped by venting the reactor. 5 ml of methanol were added to the contents of the reactor. The polymer was dried overnight under reduced pressure, giving 2.00 g of polypropylene. The results of the polymerization and the results of the polymer analysis are shown in table 1 below.

Example 5

Homopolymerization of Propene

Figure 2:
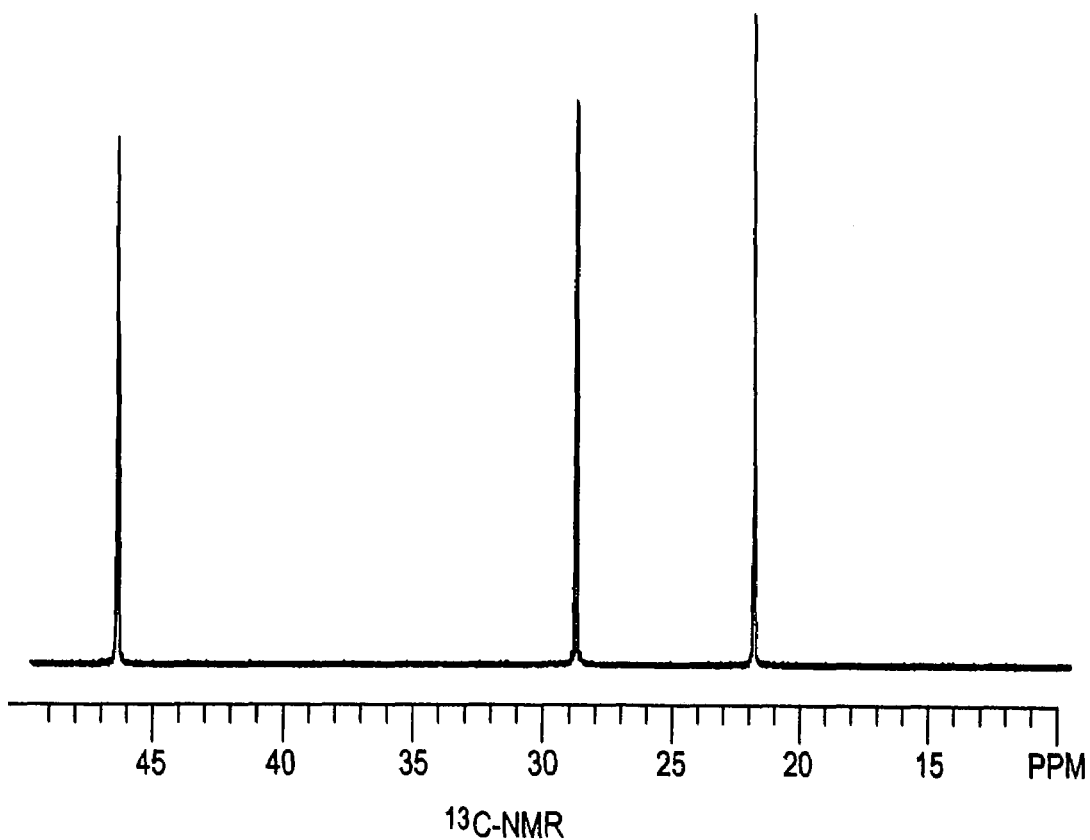

The polymerization was carried out in a manner analogous to example 4. 4 ml of a solution of triisobutylaluminum in hexane (4 mmol, 1M) together with 250 g of propylene were placed in the reactor at 30° C. and the mixture was heated to 50° C. A catalyst solution prepared by combining 10 mg of the zirconium compound (2) (14.1 µmol) from example 2 with 2.5 ml of a solution of methylaluminoxane in toluene (3.95 mmol, 10% by weight) and subsequently allowing the mixture to react for 15 minutes was introduced into the reactor together with 50 g of propylene which was at a temperature of 80° C. The contents of the reactor were stirred at 50° C. for 0.5 hour. After completion of the reaction and work-up of the polymer, 3.30 g of polypropylene were obtained. The results of the polymerization and the results of the polymer analysis are shown in table 1 below. FIG. 2 shows the $^{13}$C-NMR spectrum of the polymer. Analysis of the $^{13}$C-NMR spectrum indicated a content of mmmm pentads of 99.2%. Reverse insertions could not be detected.

Example 6

Homopolymerization of Propane (Corresponds to 00022-176)

The polymerization was carried out in a manner analogous to example 4. 4 ml of a solution of triisobutyl aluminum in hexane (4 mmol, 1M) and 5 ml of MAO (7.9 mmol, 10% by weight) together with 250 g of propylene were placed in the reactor at 30° C., 50 ml of hydrogen were added and the mixture was heated to 50° C. A catalyst solution prepared by combining 20 mg of the zirconium compound (2) (28.3 µmol) from example 2 with 3.9 ml of a solution of methylaluminoxane in toluene (6.2 mmol, 10% by weight) and subsequently allowing the mixture to react for 15 minutes was introduced into the reactor together with 50 g of propylene which had a temperature of 80° C. The reactor was heated to 70° C. and the contents of the reactor were stirred at 70° C. for 0.5 hour. After completion of the reaction and work-up of the polymer, 18 g of polypropylene were obtained. The results of the polymerization and the results of the polymer analysis are shown in table 1 below, Example 7

Homopolymerization of Propene

The polymerization was carried out in a manner analogous to example 6. 4 ml of a solution of triisobutylaluminum in hexane (4 mmol, 1M) end 5 ml of MAO (7.9 mmol, 100% by weight) together with 250 g of propylene were placed in the reactor at 30° C., 50 ml of hydrogen were added and the mixture was heated to 50° C. A catalyst solution prepared by combining 10 mg of the zirconium compound (2) (14.1 µmol) from example 2 with 3.9 ml of a solution of methylaluminoxane in toluene (6.2 mmol, 10% by weight) and subsequently allowing the mixture to react for 15 minutes was introduced into the reactor together with 50 g of propylene which had a temperature of 80° C. The reactor was heated to 70° C. and the contents of the reactor were stirred at 70° C. for 0.5 hour. After completion of the reaction and work-up of the polymer, 26 g of polypropylene were obtained. The results of the polymerization and the results of the polymer analysis are shown in table 1 below.

Example 8

Homopolymerization of Propene

The polymerization was carried out in a manner analogous to example 4. 4 ml of a solution of triisobutylaluminum in hexane (4 mmol, 1M) together with 250 g of propylene were placed in the reactor at 30° C. and the mixture was heated to 50° C. A catalyst solution prepared by combining 10 mg of (S,S)-(+)-N,N'-bis(3,5-di-tert-butylsalicylidene)-1,2-diaminocyclohexanechromium(III) chloride (15.8 µmol) with 3.3 ml of a solution of methylaluminoxane in toluene (15.8 mmol, 30% by weight) and subsequently allowing the mature to react for 15 minutes was introduced into the reactor together with 50 g of propylene which was at a temperature of 80° C. The contents of the reactor were stirred at 70° C. for 1.0 hour. After completion of the reaction and work-up of the polymer, 0.15 g of polypropylene was obtained. The results of the polymerization and the results of the polymer analysis are shown in table 1 below.

Example 9

Copolymerization of Propene with Ethylene

The polymerization was carried out in a manner analogous to example 8. 4 ml of a solution of triisobutylaluminum in hexane (4 mmol, 1M) together with 250 g of propylene were placed in the reactor at 30° C. and the mixture was heated to 50° C. A catalyst solution prepared by combining 10 mg of (S,S)-(+)-N,N'-bis(3,5-di-tert-butylsalicylidene)-1,2-diaminocyclohexanechromium(III) chloride (15.8 µmol) with 3.3 ml of a solution of methylaluminoxane in toluene (15.8 mmol, 30% by weight) and subsequently allowing the mixture to react for 15 minutes was introduced into the reactor together with 50 g of propylene which was at a temperature of 80° C. The contents of the reactor were heated to 70° C., ethylene was introduced into the reactor at a gauge pressure of 2 bar and the mixture was stirred at 70° C. for 1.0 hour. After completion of the reaction and work-up of the polymer, 1.9 g of polymer were obtained. The results of the polymerization are shown in table 1 below.

Example 10

Homopolymerization of Propene

The polymerization was carried out in a manner analogous to example 8. 4 ml of a solution of triisobutylaluminum in hexane (4 mmol, 1M) together with 250 g of propylene were placed in the reactor at 30° C. 100 ml of hydrogen were added and the mixture was heated to 50° C. A catalyst solution prepared by combining 5 mg of (S,S)-(+)-N,N'-bis(3,5-di-tert-butylsalicylidene)-1,2-diaminocyclohexanechromium (III) chloride (15.8 µmol) and 3.3 ml of a solution of methyl aluminoxane in toluene (15.8 mmol, 30% by weight) and subsequently allowing the mixture to react for 15 minutes was introduced into the reactor together with 50 g of propylene which was at a temperature of 80° C. The contents of the reactor were stirred at 70° C. for 0.5 hour. After completion of the reaction and work-up of the polymer, 4.8 g of polypropylene were obtained. The results of the polymerization are shown in table 1 below.

TABLE 1

| Example | TM | Al/TM [mol/mol] | Activity [kg/(g * h)] | Melting point [° C.] | Viscosity No. [dl/g] | $M_w$ [kg/mol] | Q |
|---|---|---|---|---|---|---|---|
| 4 | Ti | 262 | 0.4 | 158.3 | 1.8 | 502 | 6.1 |
| 5 | Zr | 280 | 0.66 | 166.3 | 4.4 | 1050 | 3.0 |
| 6 | Zr | 500 | 1.8 | 165 | 1.9 | 243 | 2.1 |
| 7 | Zr | 1000 | 5.2 | 163 | 1.5 | | |
| 8 | Cr | 1000 | 0.2 | 163.5 | | | |
| 9 | Cr | 1000 | 0.2 | | | | |
| 10 | Cr | 2100 | 1.92 | | | | |
| 12 | Zr | 3030 | 15.4 | 160 | 2.6 | 297 | 2.0 |

Units and abbreviations: Al/TM is the molar ratio of the amount of aluminum from the MAO to the amount of the transition metal complex; activity in $kg_{polymer}/(g_{transition\ metal\ compound} * h_{polymerization\ time})$; weight average molar mass determined by GPC; polydispersity Q = Mn/Mw.

Example 11

Application of (S,S)-(+)-N,N'-bis(3,5-di-tert-butylsalicylidene)-1,2-diaminocyclohexanezirconium(IV) dichloride to a support 1 g of silica gel was suspended in 15 ml of toluene. 70.3 mg of (S,S)-(+)-N,N'-bis(3,5-di-tert-butylsalicylidene)-1,2-diaminocyclohexanezirconium(IV) dichloride (2) (0.1 mmol) were added and the mixture was refluxed for 2 hours. A yellow powder was formed; the supernatant solution was colorless. Toluene was removed and the powder was dried in an oil pump vacuum for 2 hours. This gave 1.1 g of yellow powder.

Example 12

Homopolymerization of Propene

The polymerization was carried out in a manner analogous to example 4. 4 ml of a solution of triisobutylaluminum in hexane (4 mmol, 1M) together with 250 g of propylene were placed in the reactor at 30° C. and the contents of the reactor were heated to 50° C. At 50° C., 50 ml of hydrogen were added. 8.4 ml of a 30% strength solution of methylaluminoxane in toluene (40 mmol) were then injected and 0.402 g of the powder prepared in example 11 suspended in 2 ml of hexane were subsequently introduced into the reactor together with 50 g of propylene which had a temperature of 80° C. The reactor was heated to 70° C. and the contents of the reactor were stirred at 70° C. for 0.5 hour. After completion of the reaction and work-up of the polymer, 8.4 g of polypropylene having a melting point of 162.1° C. were obtained.

Example 13

Application of (S,S-(+)-N,N'-bis(3.5-di-tert-butyl-salicylidene)-1,2-diaminocyclohexanezirconium(IV) dichloride to a support 2 g of silica gel were suspended in 10 ml of toluene at room temperature and 5.2 ml of 30% strength MAO solution in toluene were slowly added dropwise. The mixture was stirred for 2 hours, filtered and the residue was dried in an oil pump vacuum for 1 hour. 56.7 mg (0.08 mmol) of (S,S)-(+)-N,N'-bis(3,5-di-tert-butylsalicylidene)-1,2-diaminocyclohexanezirconium(IV) dichloride (2) were dissolved in 8 ml of toluene, admixed with 0.9 ml of 30% strength MAO solution in toluene and the mixture was stirred for 1 hour. The silica gel which had been treated with MAO was dried, suspended in 10 ml of toluene and the solution of zirconium complex/MAO was slowly added dropwise. After stirring for 1 hour, toluene was removed and the solid was dried in an oil pump vacuum. This gave 3.19 g of a yellow, free-flowing powder.

Example 14

Homopolymerization of Propene

The polymerization was carried out in a manner analogous to example 4. 4 ml of a solution of triisobutylaluminum in hexane (4 mmol, 1M) together with 250 g of propylene were placed in the reactor at 30° C. and the contents of the reactor were heated to 50° C. At 50° C., 50 ml of hydrogen were added. 2.288 g of the powder prepared in example 13 suspended in hexane were then introduced into the reactor together with 50 g of propylene which was at a temperature of 80° C. The reactor was heated to 70° C. and the contents of the reactor were stirred at 70° C. for 0.5 hour. After completion of the reaction and work-up of the polymer, 4.3 g of polypropylene having a melting point of 151.1° C. were obtained.

We claim:

1. A process comprising polymerizing propylene in the presence of a catalyst system prepared by a process comprising reacting at least one transition metal compound of the formula (Ia) or (Ia*):

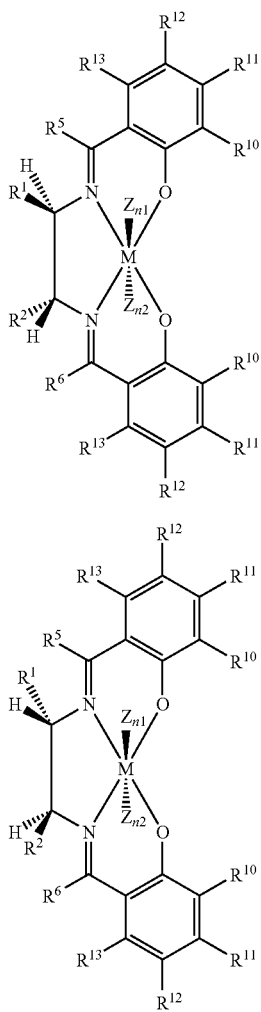

where
M is zirconium or hafnium;
Z are identical or different and are each halogen, hydrogen, $C_1$-$C_{10}$-alkyl, $C_6$-$C_{14}$-aryl, alkylaryl or arylalkyl having from 1 to 4 carbon atoms in the alkyl part and from 6 to 10 carbon atoms in the aryl part;
n1 and n2 are each 1;
$R^1$ and $R^2$ are identical or different and are each a $C_1$-$C_{40}$ radical, or $R^1$ and $R^2$ together with the atoms connecting them form a cyclic or polycyclic ring system which may contain one or more, identical or different heteroatoms selected from the group consisting of the elements N, O, P, S and Si in place of carbon atoms in the ring system;
$R^5$ and $R^6$ are identical and are each hydrogen or a $C_1$-$C_{40}$ radical;
$R^{10}$, $R^{11}$ are identical or different and are each hydrogen, t-butyl or phenyl;
$R^{12}$ are identical or different and are each t-butyl or phenyl; and
$R^{13}$ are identical or different and are each hydrogen or a $C_1$-$C_{40}$ radical, or two adjacent radicals $R^{10}$ and $R^{11}$, together with the two connecting carbon atoms may form a cyclic ring system,
with at least one cation-forming compound,
wherein an isotactic propylene polymer is formed having an isotacticity determined by pentad analysis of the $^{13}$C-NMR spectrum of greater than 98%.

2. The process of claim 1 wherein the isotactic propylene polymer comprises an isotacticity of greater than 99%.

3. The process of claim 1 wherein the isotactic propylene polymer further comprises a viscosity number greater than 1.

4. The process of claim 1 wherein the isotactic propylene polymer further comprises a melting point greater than 158° C.

5. The process of claim 4 wherein the melting point is greater than 160° C.

6. The process of claim 5 wherein the melting point is greater than 163° C.

7. The process of claim 1 wherein the isotactic propylene polymer further comprises a frequency of reverse insertions determined by pentad analysis of the $^{13}$C-NMR spectrum of less than 0.3%.

8. The process of claim 7 wherein the frequency of reverse insertions is less than 0.25%.

* * * * *